United States Patent
Goulet et al.

(10) Patent No.: US 6,852,727 B2
(45) Date of Patent: Feb. 8, 2005

(54) BENZIMISAZO[4,5-F]ISOQUINOLINONE DERIVATIVES

(75) Inventors: Joung L. Goulet, Westfield, NJ (US); Rose M. Cubbon, Fanwood, NJ (US); Richard T. Cummings, Fanwood, NJ (US); Xingfang Hong, Westfield, NJ (US); Peter J. Sinclair, Scotch Plains, NJ (US); James E. Thompson, Fanwood, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/485,720
(22) PCT Filed: Jul. 26, 2002
(86) PCT No.: PCT/US02/23876
§ 371 (c)(1),
(2), (4) Date: Jan. 30, 2004
(87) PCT Pub. No.: WO03/011285
PCT Pub. Date: Feb. 13, 2003

(65) Prior Publication Data

US 2004/0176601 A1 Sep. 9, 2004

Related U.S. Application Data

(60) Provisional application No. 60/309,364, filed on Aug. 1, 2001.

(51) Int. Cl.$^7$ ............................................... A61K 31/44
(52) U.S. Cl. ......................................... 514/287; 546/64
(58) Field of Search ............................. 546/64; 514/287

(56) References Cited

PUBLICATIONS

James E. Thompson, et al., *Bioorganic & Medicinal Chemistry Letters*, vol. 12, pp. 1219–1223, (2002).

*Primary Examiner*—Amelia A. Owens
(74) *Attorney, Agent, or Firm*—Mollie M. Yang; David L. Rose

(57) ABSTRACT

Benzimidazo[4,5-f]isoquinolinone derivatives are inhibitors of Janus protein tyrosine kinases (Jak), and as such are useful as immunosuppressants, and in the treatment of diseases including asthma, allergies, autoimmune diseases.

9 Claims, No Drawings

BENZIMISAZO[4,5-F]ISOQUINOLINONE DERIVATIVES

CROSS REFERENCE TO RELATED APPLICATIONS

This application is the National Stage of International Application No. PCT/US02/23876, filed 26 Jul. 2002, which claims the benefit under 35 U.S.C. 119(e) of U.S. Provisional Application No. 60/309,364, filed 01 Aug. 2001.

BACKGROUND OF THE INVENTION

Janus protein tyrosine kinases ("Jak"s) associate with the intracellular portions of many cytokine and growth hormone receptors. A Jak family protein kinase is characterized by seven regions of sequence homology and four family members have been identified to date: Jak1, Jak2, Jak3 and Tyk2. Jak1, Jak2 and Tyk2 are expressed almost ubiquitously whereas Jak3 appears to be expressed principally in hematopoietic cells. Jaks transduce extracellular signals by phosphorylating cytoplasmic proteins, among the best characterized of which are the signal transducers and activators of transcription ("STAT"s). The STATs dimerize on phosphorylation and directly activate transcription after nuclear translocation. These signaling events mediate such diverse biological outcomes as thymocyte development and erythrocyte differentiation.

Jak3 associates with the common gamma chain ($\gamma_c$) of the extracellular receptors for the following interleukins (IL's): IL-2, IL-4, IL-7, IL-9, IL-15. IL-4 is implicated in pathogenesis of asthma and allergic inflammation. IL-4 signaling can be disrupted by blocking Jak tyrosine kinase activity with the small molecule inhibitor AG490. Cells with genetic deficiencies in the Jaks show similar behavior: thymocytes derived from Jak1 deficient mice show an impaired responsiveness to IL-4, and T cells from Jak3 deficient mice are unresponsive to IL-4. Taken together, these data support the hypothesis that modulation of IL-4 signaling by modulation of Jak kinase activity would be beneficial to patients suffering from allergic inflammation and asthma.

A Jak3 deficiency is associated with an immune compromised (SCID) phenotype in both rodents and humans. The SCID phenotype of Jak3 −/− mammals and the lymphoid cell specific expression of Jak3 are two favorable attributes of a target for an immune suppressant. The T cells from Jak3 deficient mice did not respond to IL-2, and thymocytes derived from Jak1 deficient mice showed impaired responses to IL-2. IL-2 has a central role in regulation of T cells, and an antibody that binds to an extracellular portion of the IL-2 receptor is efficacious in preventing transplant rejection. These data suggest that inhibitors of Jak protein kinase in general and Jak3 protein kinase activity in particular could impede T-cell activation and prevent rejection of grafts following transplant surgery. Another use for these agents is to provide therapeutic benefit to patients suffering autoimmune disorders.

Constitutively active Jak2 has been found in the leukemic cells of relapsing acute lymphoblastic leukemia patients, and treatment of the leukemic cells with AG490, a tyrosine kinase inhibitor, blocks both Jak2 activity and proliferation. In addition, fusions of the Jak kinases and TEL proteins are transforming in Ba/F3 cells. Kinase inactive mutants of Jak1 introduced into bone marrow cells inhibit the ability of the oncogene v-Ab1 to activate STATs and to induce cytokine-independent proliferation. Hence inhibitors of Jak protein kinase activity may be used to treat neoplastic diseases such as leukemias.

Tyrosine kinase researchers have generated inhibitors in a variety of structural classes. Previous literature reports of Jak family inhibitor scaffolds with efficacy in mouse disease models have included benzylidenemalonitriles ("tyrphostins"), quinazolines (WHI-P154, and WHI-P151), and pyrrolo[2,3-d]-pyrimidines. No dissociation constants measured by steady state kinetic methods were reported for these inhibitors but both the tyrphostins and WHI-P151 inhibit Jak driven biological events at micromolar concentrations.

SUMMARY OF THE INVENTION

The present invention relates to inhibitors of Janus protein tyrosine kinases useful as therapeutic agents, methods for their preparation and use, and pharmaceutical compositions containing such compounds.

DETAILED DESCRIPTION OF THE INVENTION

The present invention provides compounds of formula I:

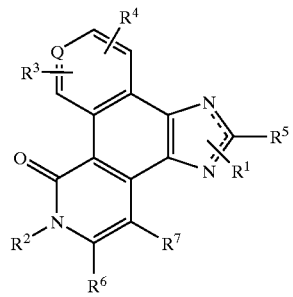

I wherein one of the ==== bond is a double bond, and the other is a single bond;

Q is N or C;

$R^1$ is attached to the nitrogen atom having the available valence, and is selected from hydrogen, $C_{1-6}$alkyl, $C_{2-6}$alkenyl, $C_{3-6}$cycloalkyl, aryl-$C_{1-3}$alkyl, and aryl wherein said alkyl, alkenyl, cycloalkyl, and aryl are optionally substituted with one to three groups independently selected from X;

$R^2$ is a group selected from $R^1$;

$R^3$, $R^4$, $R^6$ and $R^7$ are independently selected from hydrogen, X, $C_{2-6}$alkenyl and $C_{3-6}$cycloalkyl wherein said alkenyl and cycloalkyl are optionally substituted with one to three groups independently selected from X;

$R^5$ is selected from hydrogen, $C_{1-6}$alkyl, $C_{2-6}$alkenyl, Cy, and Cy-$C_{1-3}$alkyl, wherein said alkyl, alkenyl, and Cy are optionally substituted with one to three groups independently selected from X;

Cy is selected from cycloalkyl, heterocyclyl, aryl, and heteroaryl;

X is selected from:
 (a) halo,
 (b) CN,
 (c) $OR^a$,
 (d) $C_{1-6}$perfluoroalkyl,
 (e) $C(O)R^a$,
 (f) $C(O)OR^a$,
 (g) $C(O)NR^bR^c$,
 (h) $NR^bR^c$,
 (i) $NHR^bNHR^b$, (j) NHC(O)R$^a$, (k) NHC(O)OR$^a$, (l) phenyl wherein phenyl is optionally substituted with one to three groups independently selected from R$^x$, (m) C$_{1-6}$alkyl optionally substituted with OH, C$_{3-7}$cycloalkyl, phenyl, or heterocyclyl, wherein phenyl is optionally substituted with one to three groups independently selected from R$^x$, and wherein said heterocyclyl is optionally substituted with one to three groups independently selected from R$^y$, (n) heterocyclyl wherein said heterocyclyl is optionally substituted with one to three groups independently selected from R$^y$, (o) S(O)$_n$R$^a$, wherein n is 0, 1 or 2; and (p) SO$_2$NHR$^a$;

R$^a$, R$^b$ and R$^c$ are independently selected from hydrogen, C$_{1-6}$alkyl, C$_{2-6}$alkenyl, C$_{2-6}$alkynyl, Cy and Cy-C$_{1-3}$alkyl, wherein Cy is optionally substituted with one to three groups selected from R$^y$; or R$^b$ and R$^c$ together with the atom(s) to which they are attached form a heterocyclic ring of 4 to 7 members containing 0–2 additional heteroatoms independently selected from oxygen, sulfur and N—R$^e$;

R$^e$ is selected from hydrogen, C$_{1-6}$alkyl, Cy and Cy-C$_{1-3}$alkyl;

R$^x$ is selected from halo, phenyl, CN, NO$_2$, OH, OC$_{1-6}$alkyl, C$_{1-6}$alkyl, NH$_2$, NHC$_{1-6}$alkyl, N(C$_{1-6}$alkyl)$_2$, C(O)C$_{1-6}$alkyl, C(O)OC$_{1-6}$alkyl, C(O)NHC$_{1-6}$alkyl, C(O)N(C$_{1-6}$alkyl)$_2$, NHC(O)C$_{1-6}$alkyl;

R$^y$ is a group selected from R$^x$, oxo, C$_{1-6}$alkyl substituted with C$_{3-7}$cycloalkyl, and C(O)OCH$_2$-phenyl;

or a pharmaceutically acceptable salt thereof.

In one embodiment of formula I are compounds wherein R$^1$ is selected from hydrogen, C$_{1-6}$alkyl, C$_{3-6}$cycloalkyl and aryl-C$_{1-3}$alkyl wherein alkyl, cycloalkyl and aryl are optionally substituted with one or two groups independently selected from X. Examples of R$^1$ include, but are not limited to, hydrogen, methyl, ethyl, dimethylaminoethyl, cyclopropyl and benzyl.

In another embodiment of formula I, R$^3$ and R$^4$ are independently selected from hydrogen, halogen and trifluoromethyl, and when Q is C and one or both of R$^3$ and R$^4$ are other than hydrogen, one of the substituents is attached to the 9-position (ring numbering as shown below). Examples of R$^3$/R$^4$ include, but are not limited to, hydrogen/hydrogen; hydrogen/fluorine, chlorine, bromine or iodine; chlorine/chlorine; hydrogen/trifluoromethyl.

In another embodiment of formula I, R$^5$ is selected from C$_{1-6}$alkyl and Cy wherein each is optionally substituted with one to three groups independently selected from X. In one subset thereof, R$^5$ is phenyl optionally substituted with one to three groups independently selected from X. Examples or R$^5$ include, but are not limited to, methyl, ethyl, n-propyl, t-butyl, cyclopropyl, cyclobutyl, cyclopentyl, cyclohexyl, phenyl, 2- or 3- or 4-chlorophenyl, 2- or 3- or 4-fluorophenyl, 2- or 3- or 4-bromophenyl, 2- or 3- or 4-hydroxyphenyl, 2- or 3- or 4-methylphenyl, 2- or 3- or 4-methoxyphenyl, 2- or 3- or 4-trifluoromethylphenyl, 2,6-dichlorophenyl, 2,6-difluorophenyl, 2,6-dimethylphenyl, 2,6-dimethoxyphenyl, 2-fluoro-6-chlorophenyl, 2-chloro-4-hydroxyphenyl, 2- or 3- or 4-pyridyl and 3-chloro-2-thienyl, and N-benzyloxycarbonyl-4-piperidyl.

In another embodiment of formula I, Q is C. Another embodiment of formula I are compounds wherein Q is N.

Representative compounds of formula I are as follows:

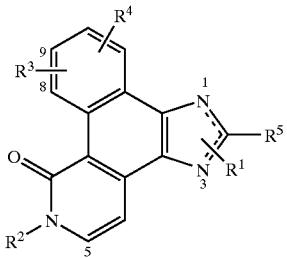

| R$^1$ | R$^2$ | R$^3$ | R$^4$ | R$^5$ |
|---|---|---|---|---|
| H | H | 9-F | H | t-butyl |
| H | CH3 | 9-F | H | t-butyl |
| 1-CH$_3$ | H | 9-F | H | t-butyl |
| 3-CH$_3$ | H | 9-F | H | t-butyl |
| H | H | 9-F | H | Phenyl |
| H | H | 9-F | H | 4-Cl-Ph |
| H | CH$_3$ | 9-F | H | 4-Cl-Ph |
| H | H | 9-F | H | 4-OCH$_3$-Ph |
| H | H | 9-F | H | Methyl |
| H | H | 9-F | H | 4-CH$_3$-Ph |
| H | H | 9-F | H | 3-Cl-Ph |
| H | H | 9-F | H | 2-CH$_3$-Ph |
| H | H | 9-F | H | 2,6-diOCH$_3$-Ph |
| H | H | 9-F | H | 2-OCH$_3$-Ph |
| H | H | 9-F | H | 2-Cl-Ph |
| H | H | 9-F | H | 2-F-Ph |
| H | H | 9-F | H | 2,6-diCl-Ph |
| H | H | 9-F | H | 2,6-diF-Ph |
| H | H | 9-F | H | c-Hex |
| H | H | 9-F | H | 2-F-6-Cl-Ph |
| H | H | 9-F | H | 2-Br-Ph |
| H | H | 9-F | H | H |
| H | H | 9-F | H | 2-OH-Ph |
| H | H | 9-F | H | 3-OH-Ph |
| H | H | 9-F | H | 4-OH-Ph |
| H | H | 9-F | H | 2-CF$_3$-Ph |
| H | H | 9-F | H | 2-Cl-4-OH-Ph |
| H | H | 9-F | H | c-Pen |
| H | H | 9-F | H | n-propyl |
| H | H | 9-F | H | 3-Cl-2-thienyl |
| H | H | 9-F | H | 3-pyridyl |
| 1-CH$_3$ | H | 9-F | H | Phenyl |
| 1-CH$_2$CH$_3$ | H | 9-F | H | Phenyl |
| 1-benzyl | H | 9-F | H | Phenyl |
| 1-diCH$_3$-N-ethyl | H | 9-F | H | Phenyl |
| 1-cPr | H | 9-F | H | Phenyl |
| 1-CH$_3$ | H | 9-F | H | 2-CH$_3$-Ph |
| 1-CH$_3$ | H | 9-F | H | 2,6-diCl-Ph |
| H | H | 9-Cl | 10-Cl | t-butyl |
| H | H | 8-Cl | 9-Cl | t-butyl |
| H | H | 9-Cl | 10-Cl | 2,6-diCl-Ph |
| H | H | 8-Cl | 9-Cl | 2,6-diCl-Ph |
| H | H | 10-CF$_3$ | H | 1-CBZ-4-piperidyl* |
| H | H | 10-CF$_3$ | H | 4-piperidyl |
| H | H | H | H | t-butyl |

*CBZ is benzyloxycarbonyl

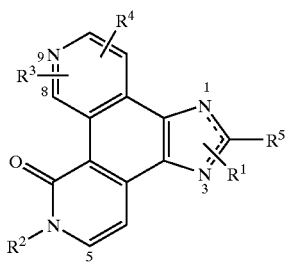

| R$^1$ | R$^2$ | R$^3$ | R$^4$ | R$^5$ |
|---|---|---|---|---|
| H | H | H | H | t-butyl |
| H | CH3 | H | H | t-butyl |
| 1-CH$_3$ | H | H | H | t-butyl |
| 3-CH$_3$ | H | H | H | t-butyl |
| H | H | H | H | Phenyl |
| H | H | H | H | 4-Cl-Ph |
| H | CH$_3$ | H | H | 4-Cl-Ph |
| H | H | H | H | 4-OCH$_3$-Ph |
| H | H | H | H | Methyl |
| H | H | H | H | 4-CH$_3$-Ph |
| H | H | H | H | 3-Cl-Ph |
| H | H | H | H | 2-CH$_3$-Ph |
| H | H | H | H | 2,6-diOCH$_3$-Ph |
| H | H | H | H | 2-OCH$_3$-Ph |
| H | H | H | H | 2-Cl-Ph |
| H | H | H | H | 2-F-Ph |
| H | H | H | H | 2,6-diCl-Ph |
| H | H | H | H | 2,6-diP-Ph |
| H | H | H | H | c-Hex |
| H | H | H | H | 2-F-6-Cl-Ph |
| H | H | H | H | 2-Br-Ph |
| H | H | H | H | H |
| H | H | H | H | 2-OH-Ph |
| H | H | H | H | 3-OH-Ph |
| H | H | H | H | 4-OH-Ph |
| H | H | H | H | 2-CF$_3$-Ph |
| H | H | H | H | 2-Cl-4-OH-Ph |
| H | H | H | H | c-Pen |
| H | H | H | H | n-propyl |
| H | H | H | H | 3-Cl-2-thienyl |
| H | H | H | H | 3-pyridyl |
| 1-CH$_3$ | H | H | H | Phenyl |
| 1-CH$_2$CH$_3$ | H | H | H | Phenyl |
| 1-benzyl | H | H | H | Phenyl |
| 1-diCH$_3$-N-ethyl | H | H | H | Phenyl |
| 1-cPr | H | H | H | Phenyl |
| 1-CH$_3$ | H | H | H | 2-CH$_3$-Ph |
| 1-CH$_3$ | H | H | H | 2,6-diCl-Ph |
| H | H | H | 10-Cl | t-butyl |
| H | H | 8-Cl | H | t-butyl |
| H | H | H | 10-Cl | 2,6-diCl-Ph |
| H | H | 8-Cl | H | 2,6-diCl-Ph |
| H | H | H | 10-CF$_3$ | 4-piperidyl |

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to inhibit Jaks activity, particularly Jak3 activity, makes them useful for preventing or reversing the symptoms, disorders or diseases induced by the activation of Jaks, such as allergic disorders, asthma, autoimmune and other immune associated disorders; these compounds are also useful as immunosuppressants to prevent transplant rejections. Allergic disorders include Type I immediate hypersensitivity reactions such as allergic rhinitis hay fever), allergic urticaria (hives), angioedema, allergic asthma and anaphylaxis, i.e., "anaphylactic shock." Autoinmmune diseases include systemic lupus erythematosis (SLE), myasthenia gravis, diabetes, rheumatoid arthritis, and Grave's disease. Compound of Formula I are also useful for the treatment of neoplastic diseases such as leukemias and lymphomas.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lies within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) antileukotriene agents including, without limitation, leukotriene D4 receptor antagonists such as zafirlukast, montelukast, pranlukast, iralukast, pobilukast and SKB-106,203, and leukotriene biosynthesis inhibitors such aszileuton and BAY-1005; (b) VLA-4 antagonists; (c) intranasal, inhaled and oral steroids such as beclomethasone, fluticasone, mometasone, flunisolide, budesonide, prednisolone, methylprednisolone, betamethasone, prednisone, dexamethasone, triamcinolone, and hydrocortisone; (d) immunosuppressants including calcineurin inhibitors such as cyclosporin and tacrolimus, rapamycin and other TOR protein inhibitors, purine biosynthesis inhibitors; (e) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (f) beta agonists such as terbutaline, metaproterenol, fenoterol, isoetharine, albuterol, bitolterol, salmeterol and pirbuterol; (g) other drugs for asthma and chronic obstructive pulmonary diseases such as theophylline, cromolyn sodium, atropine, ipratropium bromide, and tiotropium bromide; (h) inhibitors of phosphodiesterase type IV (PDE-IV) such as cilomilast and roflumilast; (i) antagonists of the chemokine receptors, especially CCR-1, CCR-2, and CCR-3; (j) PGD2 receptor antagonists; and (k) antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used.

Compounds of the present invention may be prepared by procedures illustrated in the accompanying schemes.

Several methods for preparing the compounds in this invention are illustrated in the following Schemes and Examples. Starting materials are made from known procedures or as illustrated.

of Formula I. Ketones 1-5 can be synthesized by reacting suitably substituted amides 1-2 or readily available esters 1-3 with commercially available 2-fluoro-4-methylpyridine 1-4 using a base such as sodium bis(trimethylsilyl)amide, lithium bis(trimethylsilyl)amide, lithium diisopropylamide, n-butyllithium, sec-butyllithium, potassium t-butoxide, and other suitable bases. N-methyl-N-methoxyamides 1-2 can be prepared from commercially available acids 1-1 and N,O-dimethylhydroxylamine under standard coupling reaction conditions.

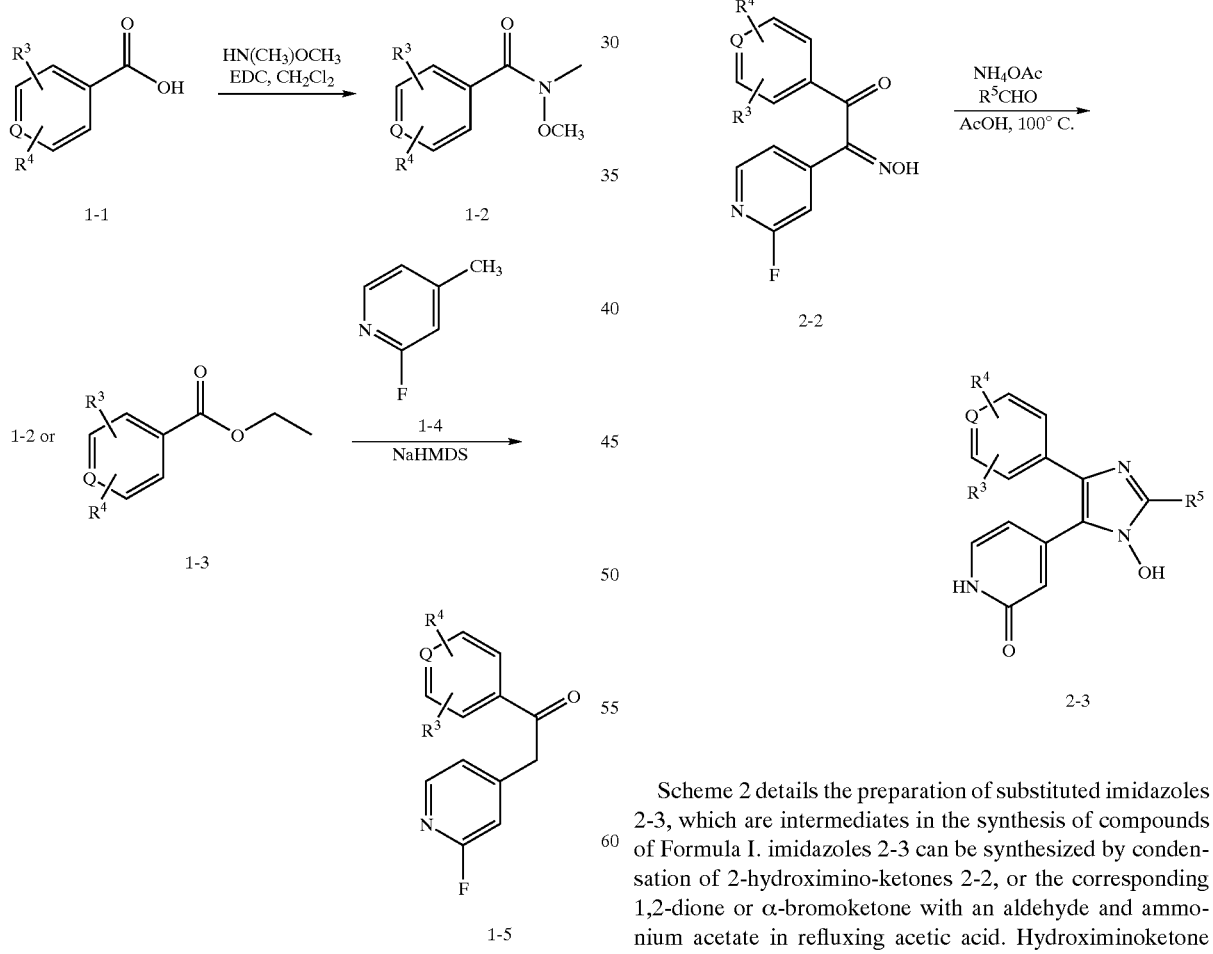

Scheme 1 details the preparation of substituted ketoness 1-5 which are intermediates in the synthesis of compounds Scheme 2 details the preparation of substituted imidazoles 2-3, which are intermediates in the synthesis of compounds of Formula I. imidazoles 2-3 can be synthesized by condensation of 2-hydroximino-ketones 2-2, or the corresponding 1,2-dione or α-bromoketone with an aldehyde and ammonium acetate in refluxing acetic acid. Hydroximinoketone 2-2 can be obtained by treatment of substituted ketone 2-1 with tert-butylnitrite in ethanol, methanol, isopropanol or other suitable solvents.

SCHEME 3

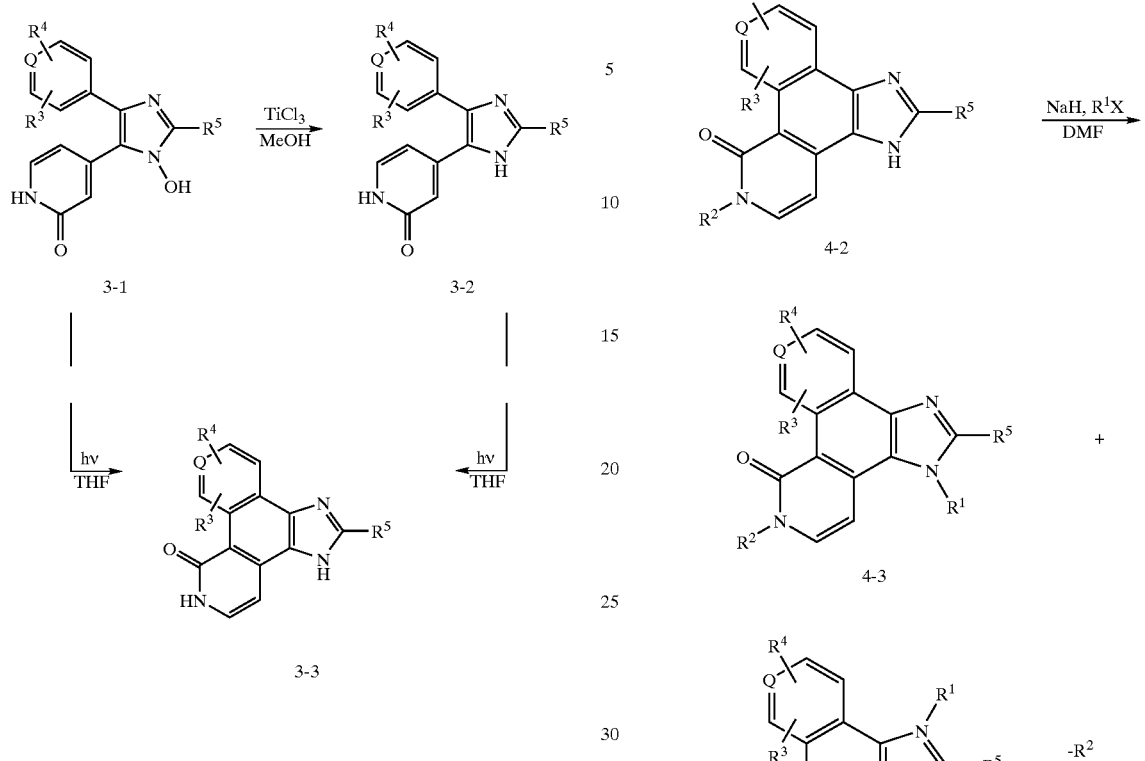

The preparation of benzo- or pyrido-fused imidazo[4,5-f]isoquinolin-7-one 3-3 is detailed in Scheme 3. Substituted N-hydroxyimidazole 3-1 can be treated with titanium trichloride or other reducing agent, such as phosphorous trichloride, in methanol or other suitable solvent such as chloroform, dichloromethane, ethanol, isopropanol, or tert-butanol at room temperature to afford substituted imidazole 3-2. Upon UV irradiation of 3-2 in solvents such as tetrahydrofuran, methanol, dichloromethane or the like substituted benzo- or pyrido-fused imidazo[4,5-f]isoquinolin-7-one 3-3 can be obtained. Alternatively, benzo- or pyrido-fused imidazo[4,5-f]isoquinolin-7-ones 3-3 can be directly obtained from substituted N-hydroxyimidazole 3-1 by UV irradiation of 3-1 in a solvent such as tetrahydrofuran, methanol, dichloromethane or the like.

Scheme 4

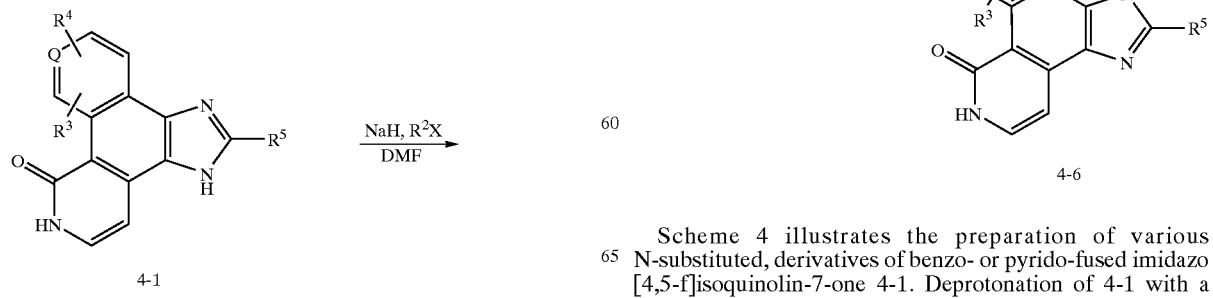

Scheme 4 illustrates the preparation of various N-substituted, derivatives of benzo- or pyrido-fused imidazo [4,5-f]isoquinolin-7-one 4-1. Deprotonation of 4-1 with a base such as sodium hydride, lithium diisopropylamide, potassium hydride, lithium bis(trimethylsilyl)amide, sodium hydroxide, potassium hydroxide or the like followed by the addition of an electrophile such as an alkyl halide, alkyl mesylate, alkyl tosylate, acyl halide, acid anhydride or the like, affords a compound of structure 4-2. Compound 4-2 can be further substituted by deprotonation, followed by alkylation or acylation as described above to afford 4-3 and 4-4 as a separable mixture of isomers. Further, $R^2$ may be selectively removed to afford compounds of structures 4-5 and 4-6.

The two nitrogen atoms of the imidazole ring may be selectively and separately derivatized as described in Schemes 5 and 6.

In Scheme 5, the condensation of a hydroximinoketone 5-1 with an aldehyde and a primary amine in refluxing acetic acid provides the N-oxo-imidazole 5-2. Upon reduction of N-oxo-imidazole 5-2 with phosphorous trichloride or other reagent such as titanium trichloride in solvents such as chloroform, dichloromethane, methanol, ethanol, isopropanol or the like, an N-substituted imidazole is obtained, which upon UV irradiation in solvents such as tetrahydrofuran, methanol, dichloromethane or the like provides imidazo[4,5-f]isoquinolin-7-one 5-4.

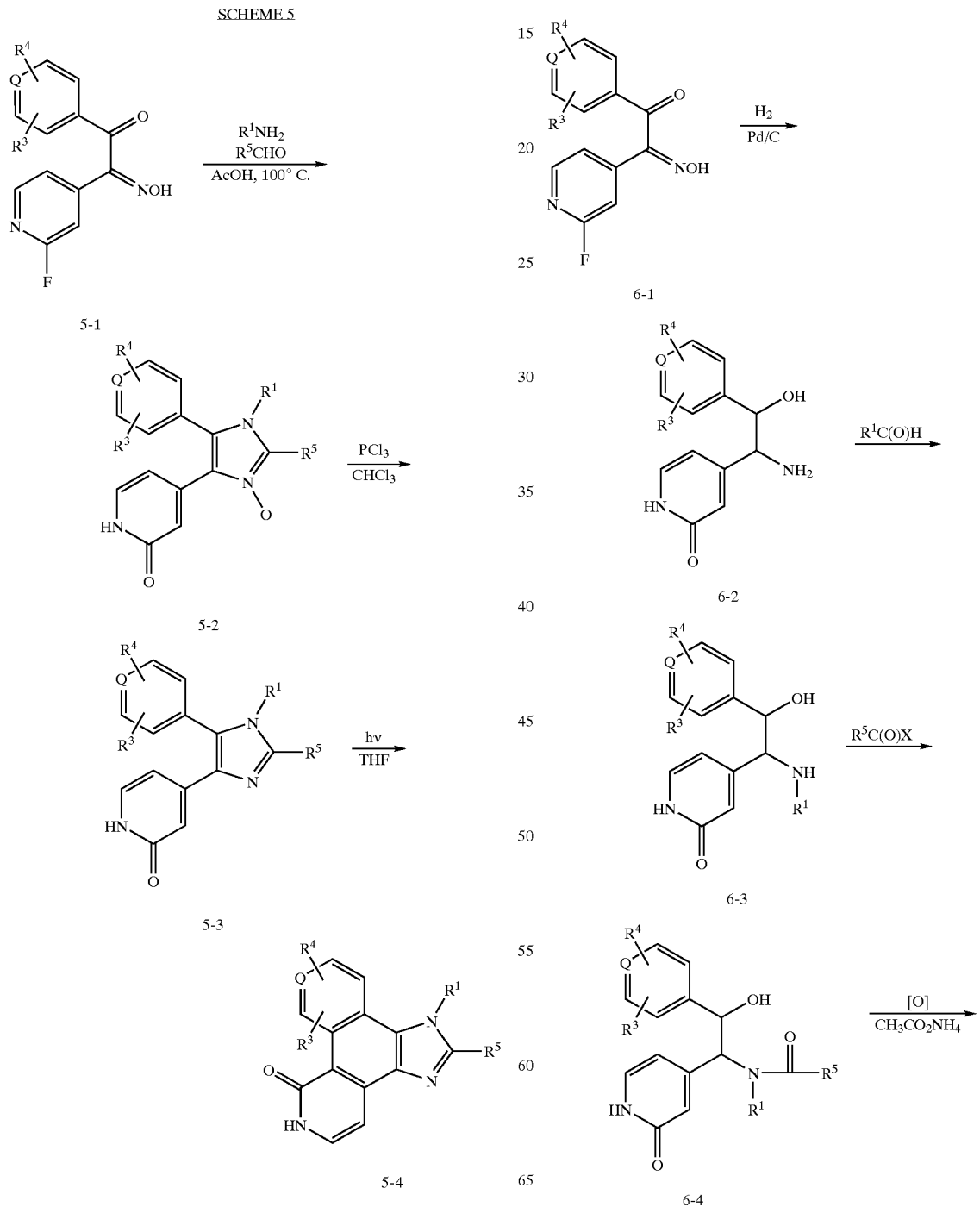

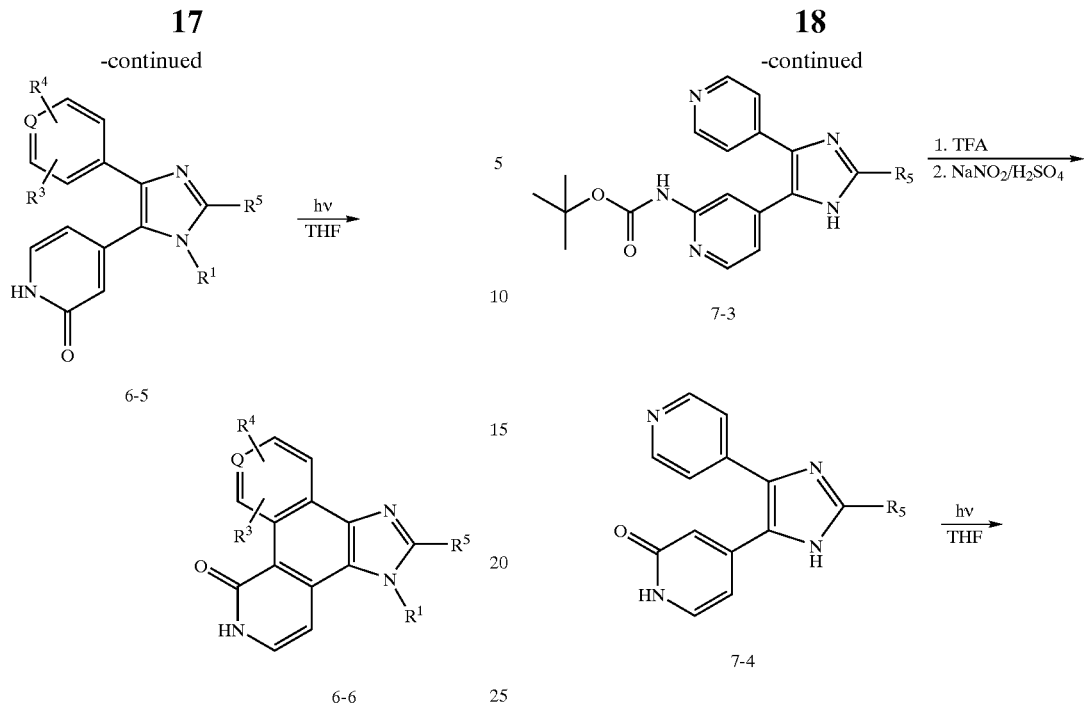

6-5

6-6

7-3

7-4

7-5

In Scheme 6, an oxime of structure 6-1 can be reduced to the corresponding amino alcohol 6-2 by hydrogenation over a suitable catalyst such as palladium on carbon in an appropriate solvent such as methanol, ethanol, ethyl acetate, THF or the like. Condensation of 6-2 with an aldehyde under standard reducing conditions affords alkylamine 6-3. Alternatively, amine 6-2 may be acylated and the resulting amide reduced to afford 6-3. Acylation of 6-3 with an acylating agent $R^5C(O)X$ such as acid chloride, acid anhydride, or carboxylic acid in the presence of a coupling reagent such as DCC, EDC or the like affords amide 6-4. Oxidation of the alcohol to the ketone followed by condensation with ammonium acetate in acetic acid affords the substituted imidazole 6-5, which upon UV irradiation in a solvent such as tetrahydrofuran, methanol, dichloromethane or the like produces the imidazo[4,5-f]isoquinolin-7-one 6-6.

SCHEME 7

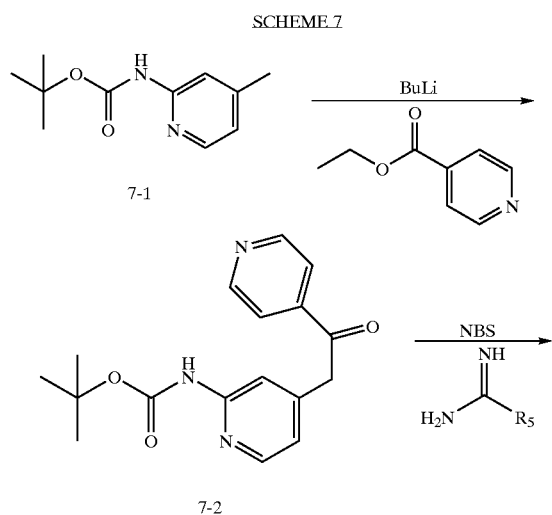

7-1

7-2

Scheme 7 details the preparation of pyrido-fused-imidazo [4,5-f]isoquinolin-7-one 7-5. Tert-butyl 4-methyl-2-pyridinylcarbamate 7-1 (Ihle, N. C.; Krause, A. E.; J. Org. Chem 1996, 61 (14), 4810–4811.) is deprotonated with butyl lithium and condensed with ethyl isonicotinate to give ketone 7-2. Bromination with NBS followed by condensation with an amidine affords imidazoles 7-3. Cleavage of the tert-butyl carbamate with TFA followed by diazotization and hydrolysis yields the pyridone substituted imidazoles 7-4. Pyrido-fused-imidazo[4,5-f]isoquinolin-7-one 7-5 can then be obtained upon UV irradiation of 7-4 in solvents such as tetrahydrofuran, methanol, dichloromethane or the like.

The following examples are provided to illustrate the invention and are not to be construed as limiting the scope of the invention in any manner.

HPLC Conditions

LC 1. Retention time using the following conditions: Column: YMC ODS A, 5 m, 4.6×50 mm; Gradient Eluent: 10:90 to 95:5 v/v acetonitrile/water+0.05% TFA over 4.5 min; Detection: PDA, 200–600 nm; Flow Rate: 2.5 mL/min.

LC 2. Retention time using the following conditions: Column: YMC Pro-C18, 5 m, 4.6×50 mm; Gradient Eluent: 10:90 to 95:5 v/v acetonitrile/water+0.05% TFA over 3.0 min; Detection: PDA, 200–600 nm; Flow Rate: 2.5 mL/min.

EXAMPLE 1

2-tert-butyl-9-fluoro-3,6-dihydro-7H-benzo[h]imidazo[4,5-f]isoquinolin-7-one

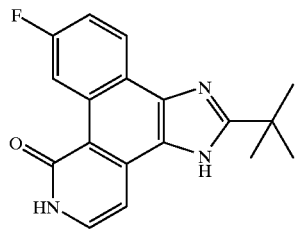

Step A: 1-(4-fluorophenyl)-2-(2-fluoropyridin-4-yl)ethanone

To a solution of sodium bis(trimethylsilyl)amide (0.465 L, 1M) in TBF (765 mL) under nitrogen, cooled to 2° C., was added 2-fluoro-4-methylpyridine (25 g, 0.225 mol) and the solution stirred for 45 minutes in an ice bath. Ethyl 4-fluorobenzoate (35 mL, 0.239 mol) was added and the reaction was stirred for 1.5 hours at RT. The reaction mixture was poured into excess aqueous 2N HCl, and the aqueous layer was made basic with 5 N NaOH and extracted with EtOAc. The organic extracts were combined, washed with brine, dried over $MgSO_4$, filtered and concentrated under reduced pressure. The residue was dissolved in $CH_2Cl_2$ and filtered through a cotton plug. Hexanes were added and the $CH_2Cl_2$ was removed under reduced pressure until precipitation of the title compound occurred as a pale yellow solid (43.2 g).

$^1$H NMR ($CDCl_3$, 500 MHz): δ 8.19 (brs, 1H), 8.04 (s, 2H), 7.19 (m, 2H), 7.09 (s, 1H), 6.86 (s, 1H), 4.32 (s, 2H). MS(ES) 234.2 (M+1); LC 1: 2.81 min.

Step B: 1-(4-fluorophenyl)-2-(2-fluoropyridin-4-yl)ethane-1,2-dione 2-oxime

To a solution of 1-(4-fluorophenyl)-2-(2-fluoropyridin-4-yl)ethanone (43 g, 0.184 mol) in ethanol (800 mL) at −10° C. was added dropwise t-butylnitrite (24.1 mL, 0.20 mol) over 10 minutes followed by 2.5 M HCl in absolute ethanol (60 mL, 0.15 mol). The reaction temperature was maintained at −5° C. during these additions. After addition was complete, the dry ice bath was removed and the reaction was allowed to warm to RT and stirred overnight. The ethanol was removed under reduced pressure and the residue was diluted with $H_2O$ and made basic with saturated $NaHCO_3$. It was extracted with EtOAc, the combined organic extracts were washed with brine, dried over $Na_2SO_4$ and concentrated under reduced pressure. The crude residue was taken up in methanol/isopropanol and mixed with toluene. The methanol/isopropanol mixture was concentrated under reduced pressure and the title compound was recrystallized from hexane/toluene (47.5 g).

$^1$H NMR ($CD_3OD$, 500 MHz): δ 7.95–8.27 (m, 3H), 7.10–7.47 (m, 4H). MS(ES) 263.1 (M+1); LC 1: 2.83 min.

Step C: 4-[2-tert-butyl-4-(4-fluorophenyl)-1-hydroxy-1H-imidazol-5-yl]pyridin-2(1H)-one To a solution of 1-(4-fluorophenyl)-2-(2-fluoropyridin-4-yl)ethane-1,2-dione 2-oxime (47.3 g, 0.18 mol) in acetic acid (1 L) under nitrogen was added trimethylacetaldehyde (21.6 mL, 0.19 mol) followed by ammonium acetate (277.5 g, 3.6 mol) and then it was heated to reflux for three hours. The acetic acid was removed under reduced pressure and the remaining material was taken up in water. The pH of the solution was adjusted to 8–10 by addition of solid ammonium hydroxide and was extracted with EtOAc. The solvent was removed under reduced pressure and the crude product was dissolved in methanol with sufficient ethanol added to effect dissolution. The solvent was removed under reduced pressure; the product was twice dissolved in ethanol and concentrated to a small volume under reduced pressure to azeotropically remove water. The title compound was recrystallized from ethanol and hexane (28.8 g).

$^1$H NMR (DMSO-$d_6$, 500 MHz): δ 11.55 (s, 1H), 11.34 (s, 1H), 7.45 (m, 2H), 7.32 (s, 1H), 7.09 (m, 2H), 6.41 (br s, 1H), 6.02 (br s, 1H), 1.37 (s, 9H). MS(ES) 328.1 (M+1)); LC1: 1.57 min.

Step D: 4-[2-tert-butyl-4-(4-fluorophenyl)-1H-imidazol-5-yl]pyridin-2(1H)-one

To a solution of 4-[2-tert-butyl-4-(4-fluorophenyl)-1-hydroxy-1H-imidazol-5-yl]pyridin-2(1H)-one (28 g, 0.086 mol) in methanol (1 L) at 0° C. under nitrogen was added $TiCl_3$ (10% w/w in 20% w/w HCl, 450 ml) over 45 minutes while maintaining the reaction temperature under 10° C. The solution was warmed to RT and stirred overnight. The methanol was removed under reduced pressure and the solution was made basic with saturated $NaHCO_3$ and 5 N NaOH. Ethyl acetate was added and it was stirred for 4 hours. The solution was filtered through a Solka floc pad to remove the solids. The filtrate was extracted with EtOAc and the organic layer was then washed twice with brine, dried over $Na_2SO_4$ and concentrated to dryness to yield crude product. It was purified by flash chromatography using $CH_2Cl_2$/2%–10% methanol as an eluant to yield the title compound as a mixture of imidazole tautomers.

$^1$H NMR (DMSO-$d_6$, 500 MHz) of the major tautomer: δ 12.05 (s, 1H); 11.25 (br s, 1H); 7.47 (m, 2H); 7.28 (m, 2H); 7.17 (m, 1H); 6.32 (d, J=1.4 Hz, 1H); 6.23 (dd, $J_1$=6.8 Hz, $J_2$=1.8 Hz, 1H); 1.33 (s, 9H). MS(ES) 312.2 (M+1)); LC 1: 1.49 min.

Step E: 2-tet-butyl-9-fluoro-3,6-dihydro-7H-benzo[h]imidazo[4,5-f]isoquinolin-7-one To 4-[2-tert-butyl-4-(4-fluorophenyl)-1H-imidazol-5-yl]pyridin-2(1H)-one (2.0 g, 6.4 mmol) in a Pyrex vessel was added TBF (2 L) and the solution was irradiated with stirring with light >350 nm for 45 minutes. During irradiation, the solution transiently turned a reddish pink; the color disappeared on further stirring without irradiation. At this juncture, further irradiation did not reinitiate the reaction. Two more batches were treated identically. The solvent was removed under reduced pressure. The crude material was purified by flash chromatography on silica gel using TBF/toluene (3/7→7/3) as an eluant. The title compound (2.6 g) was obtained as a mixture of imidazole tautomers following recrystallization from methanol.

$^1$H NMR (DMSO-$d_6$, 500 MHz) of the major tautomer: δ 12.84 (s, 1H); 11.59 (s, 1H); 10.05 (m, 1H); 8.55 (m, 1H); 7.60 (m, 1H); 7.51 (br s, 1H); 7.25 (br s, 1H); 3.32 (s, 9H). MS(ES) 310.2 (M+1); LC 1: 1.81 min.

EXAMPLE 2

2-tert-butyl-9-fluoro-6-methyl-3,6-dihydro-7H-benzo[h]imidazo[4,5-f]isoquinolin-7-one

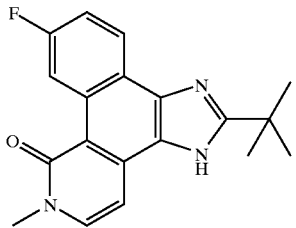

To a stirred solution of 2-tert-butyl-9-fluoro-3,6-dihydro-7H-benzo[h]imidazo[4,5-f]isoquinolin-7-one (40 mg, 0.129 mmol) in dry DMF (1.5 mL) at 0° C. was added NaH (60 wt. %) (6 mg, 0.15 mmol). After stirring for 5 minutes, iodomethane (9 μL, 0.142 mmol) was added, and the reaction mixture was slowly warmed to room temperature over 2 h. The mixture was cooled in ice bath and the reaction was quenched with water. The reaction mixture was diluted with EtOAc, washed with water followed by brine, then dried over $Na_2SO_4$. After removal of the solvent the crude was purified by preparative thin layer chromatography (1:9 MeOH:$CH_2Cl_2$ as eluent) to obtain the title compound as a mixture of imidazole tautomers.

$^1$H NMR (DMSO-$d_6$, 500 MHz) of the major tautomer: δ 12.9 (s, 1H); 10.08 (dd, $J_1$=14.2 Hz, $J_2$=2.7 Hz, 1H); 8.6 (dd, $J_1$=8.8 Hz, $J_2$=6.6 Hz, 1H); 7.89 (d, J=7.1 Hz, 1H); 7.6 (dt, $J_1$=8.7 Hz, $J_2$=2.8 Hz, 1H); 7.28 (d, J=7.1 Hz, 1H); 3.64 (s, 3H); 1.5 (s, 9H). MS(ES) 324 (M+1); LC 1: 1.46 min.

EXAMPLE 3

2-tert-butyl-9-fluoro-1-methyl-1,6-dihydro-7H-benzo[h]imidazo[4,5-f]isoquinolin-7-one and 2-tert-butyl-9-fluoro-3-methyl-3,6-dihydro-7H-benzo[h]imidazo[4,5-f]isoquinolin-7-one

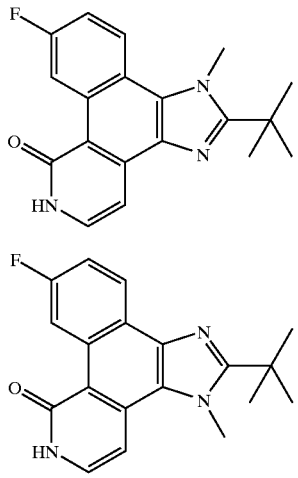

Step A: 2-tert-butyl-9-fluoro-6-{[2-(trimethylsilyl)ethoxy]methyl}-3,6-dihydro-7H-benzo[h]imidazo[4,5-f]isoquinolin-7-one The title compound was prepared according to the procedure described in EXAMPLE 2 using 2-(trimethylsilyl)ethoxymethyl chloride MS(ES) 440 (M+1); LC 1: 2.26 min.

Step B: 2-tert-butyl-9-fluoro-1-methyl-6-{[2-(trimethylsilyl)ethoxy]methyl}-1,6-dihydro-7H-benzo[h]imidazo[4,5-f]isoquinolin-7-one (isomer A) 2-tert-butyl-9-fluoro-3-methyl-6-{[2-(trimethylsilyl)ethoxy]methyl}-3,6-dihydro-7H-benzo[h]imidazo[4,5-f]isoquinolin-7-one (isomer B)

The title compounds were prepared as regioisomers and separated according to the procedure described in EXAMPLE 2.

Isomer A: $^1$H NMR (CDCl$_3$, 500 MHz): δ 10.29 (dd, J=2.7, 13.7 Hz, 1H); 8.42 (dd, J=6.0, 9.2 Hz, 1H); 7.60 (d, J=7.4 Hz, 1H); 7.55 (d, J=7.4 Hz, 1H); 7.38 (m, 1H); 5.59 (s, 2H); 4.38 (s, 3H); 3.70 (dd, $J_1$=$J_2$=8.2 Hz, 2H); 1.65 (s, 9H); 0.98 (dd, $J_1$=$J_2$=8.2 Hz, 2H); −0.02 (s, 9H).

Isomer B: $^1$H NMR (CDCl$_3$, 500 MHz): δ 10.01 (dd, $J_1$=14.2, $J_2$=2.5 Hz, 1H); 8.73 (dd, $J_1$=8.9, $J_2$=6.5 Hz, 1H); 7.52 (d, J=7.5 Hz, 1H); 7.42 (m, 1H); 7.22 (d, J=7.5 Hz, 1H); 5.57 (s, 2H); 4.32 (s, 3H); 3.71 (dd, $J_1$=$J_2$=8.2 Hz, 2H); 1.66 (s, 9H); 0.99 (dd, $J_1$=$J_2$=8.2 Hz, 2H); 0.0 (s, 9H).

Step C: 2-tert-butyl-9-fluoro-1-methyl-1,6-dihydro-7H-benzo[h]imidazo[4,5-f]isoquinolin-7-one and 2-tert-butyl-9-fluoro-3-methyl-3,6-dihydro-7H-benzo[h]imidazo[4,5-f]isoquinolin-7-one To a solution of 2-tert-butyl-9-fluoro-1-methyl-6-{[2-(trimethylsilyl)-ethoxy]methyl}-1,6-dihydro-7H-benzo[h]imidazo[4,5-f]isoquinolin-7-one (isomer A) (17 mg, 0.037 mmol) in THF (1.0 mL) was added tetrabutylammonium fluoride (75 μL, 1.0 M in THF) at room temperature, then it was heated at 60° C. for 3 h. The solvent was removed in vacuo, and the crude residue was purified by preparative thin layer chromatography (5% MeOH/$CH_2Cl_2$ as an eluent) to obtain the title compound.

$^1$H NMR (DMSO-$d_6$, 500 MHz): δ 11.65 (brs, 1H); 10.25 (dd, $J_1$=14.2 Hz, $J_2$=2.9 Hz, 1H); 8.65 (dd, $J_1$=9.0 Hz, $J_2$=6.0 Hz, 1H); 7.56 (m, 1H); 7.54 (d, J=6.6 Hz, 1H); 7.30 (d, J=6.6 Hz, 1H); 4.38 (s, 3H); 1.56 (s, 9H). MS(ES) 324 (M+1); LC 1: 1.55 min.

Similarly, starting from isomer B of Step B, 2-tert-butyl-9-fluoro-3-methyl-3,6-dihydro-7H-benzo[h]imidazo[4,5-f]isoquinolin-7-one was prepared.

$^1$H NMR (DMSO-$d_6$, 500 MHz): δ 11.81 (brs, 1H); 10.05 (dd, $J_1$=14.4 Hz, $J_2$=2.7 Hz, 1H); 8.58 (dd, $J_1$=8.9 Hz, $J_2$=6.6 Hz, 1H); 7.57 (d, J=7.4 Hz, 1H); 7.52 (m, 1H); 7.37 (d, J=7.4 Hz, 1H); 4.32 (s, 3H); 1.58 (s, 9H). MS(ES) 324 (M+1); LC 1: 1.46 min.

EXAMPLE 4

9-fluoro-2-phenyl-3,6-dihydro-7H-benzo[h]imidazo[4,5-f]isoquinolin-7-one

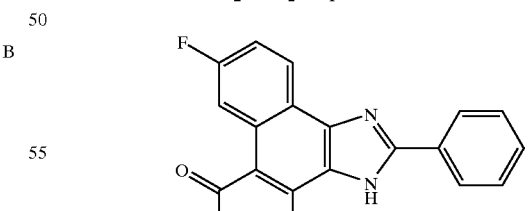

Step A: 4-[4-(4-fluorophenyl)-1-hydroxy-2-phenyl-1H-imidazol-5-yl]pyridin-2(1H)-one The title compound was prepared from 1-(4-fluorophenyl)-2-(2-fluoro-pyridin-4-yl)ethane-1,2-dione 2-oxime (EXAMPLE 1, Step B) following the procedure described in EXAMPLE 1, Step C (replacing trimethylacetaldehyde with benzaldehyde).

Mass spectrum (LC-MS, ES+): 348.1 (M+1), LC 1: 1.30 min. $^1$H NMR (CD$_3$OD, 500 MHz): δ 8.12 (d, J=7.3 Hz, 2H); 7.56–7.44 (aromatic Hs, 5H); 7.41 (d, J=6.6 Hz, 1H); 7.14 (d, J=8.9 Hz, 1H); 7.13 (d, J=8.7 Hz, 1H); 6.73 (d, J=1.3 Hz, 1H); 6.47 (dd, J$_1$=6.6 Hz, J$_2$=1.6 Hz, 1H).

Step B: 4-[4-(4-fluorophenyl)-2-phenyl-1H-imidazol-5-yl]pyridin-2(1H)-one

The title compound was prepared from 4-[4-(4-fluorophenyl)-1-hydroxy-2-phenyl-1H-imidazol-5-yl]pyridin-2(1H)-one of Step A following the procedure described in EXAMPLE 1, Step D.

Mass spectrum (LC-MS, ES+): 332.1 (M+1), LC 1: 1.18 min. $^1$H NMR (CDCl$_3$, 500 Hz): δ 8.00 (d, J=7.6 Hz, 2H); 7.54–7.35 (aromatic Hs, 5H); 7.14 (d, J=6.8 Hz, 1H); 7.09 (d, J=8.7 Hz, 1H); 7.07. (d, J=8.7 Hz, 1H); 6.75 (d, J=1.6 Hz, 1H); 6.36 (brs, 1H).

Step C: 9-fluoro-2-phenyl-3,6-dihydro-7H-benzo[h]imidazo[4,5-f]isoquinolin-7-one The title compound was prepared from 4-[4-(4-fluorophenyl)-2-phenyl-1H-imidazol-5-yl]pyridin-2(1H)-one of Step B following the procedure described in EXAMPLE 1, Step E.

Mass spectrum (LC-MS, ES+): 330.1 (M+1), LC 1: 1.56 min. $^1$H NMR (DMSO-d$_6$, 500 MHz): δ 10.05 (brd, 1H); 8.65 (dd, J$_1$=8.7 Hz, J$_2$=6.4 Hz, 1H); 8.31 (d, J=7.6 Hz, 2H); 7.66–7.48 (aromatic Hs, 5H); 7.37 (d, J=6.7 Hz, 1H).

EXAMPLE 5

2-(4-chlorophenyl)-9-fluoro-3,6-dihydro-7H-benzo[h]imidazo[4,5-f]isoquinolin-7-one

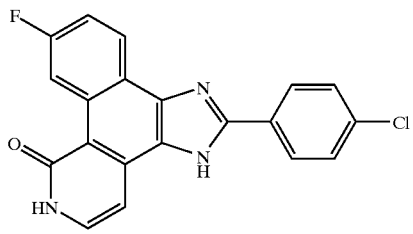

Step A: 4-[2-(4-chlorophenyl)-4-(4-fluorophenyl)-1-hydroxy-1H-imidazol-5-yl]pyridin-2(1H)-one The title compound was prepared from 1-(4-fluorophenyl)-2-(2-fluoro-pyridin-4-yl)ethane-1,2-dione 2-oxime (EXAMPLE 1, Step B) following the procedure described in EXAMPLE 1, Step C (replacing trimethylacetaldehyde with 4-chlorobenzaldehyde).

Mass spectrum (LC-MS, ES+): 382.1 (M+1), LC 1: 1.63 min. $^1$H NMR (CD$_3$OD, 500 MHz): δ 8.23 (d, J=8.7 Hz, 2H); 7.50–7.38 (aromatic Hs, 4H); 7.32 (d, J=6.9 Hz, 1H); 7.09 (d, J=8.9 Hz, 1H); 7.07 (d, J=8.7 Hz, 1H); 6.74 (s, 1H); 6.58 (d, J=6.9 Hz, 1H).

Step B: 4-[2-(4-chlorophenyl)-4-(4-fluorophenyl)-1H-imidazol-5-yl]pyridin-2(1H)-one The title compound was prepared from 4-[2-(4-chlorophenyl)-4-(4-fluorophenyl)-1-hydroxy-1H-imidazol-5-yl]pyridin-2(1H)-one of Step A following the procedure described in EXAMPLE 1, Step D.

Mass spectrum (LC-MS, ES+): 366.1 (M+1), LC 1: 1.48 min. $^1$H NMR (CD$_3$OD, 500 MHz): δ 7.98 (d, J=8.5 Hz, 2H); 7.58–7.47 (m, 4H); 7.36 (d, J=6.6 Hz, 1H); 7.22 (t, 2H); 6.71 (s, 1H); 6.55 (brs, 1H).

Step C: 2-(4-chlorophenyl)-9-fluoro-3,6-dihydro-7H-benzo[h]imidazo[4,5-f]isoquinolin-7-one The title compound was prepared from 4-[2-(4-chlorophenyl)-4-(4-fluorophenyl)-1H-imidazol-5-yl]pyridin-2(1H)-one of Step B following the procedure described in EXAMPLE 1, Step E.

Mass spectrum (LC-MS, ES+): 364.1 (M+1), LC 1: 2.04 min. $^1$H NMR (DMSO-d$_6$, 500 MHz): δ 10.05 (d, J=13.7 Hz, 1H); 8.64 (dd, J$_1$=8.9 Hz, J$_2$=6.4 Hz, 1H); 8.32 (d, J=8.5 Hz, 2H); 7.69 (d, J=8.5 Hz, 2H); 7.63 (brs, 2H); 7.35 (d, J=6.8 Hz, 1H).

EXAMPLE 6

2-(4-chlorophenyl)-9-fluoro-6-methyl-3,6-dihydro-7H-benzo[h]imidazo[4,5-f]isoquinolin-7-one

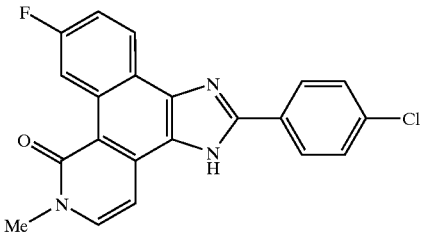

Step A: 4-[2-(4-chlorophenyl)-4-(4-fluorophenyl)-1-methoxy-1H-imidazol-5-yl]-1-methylpyridin-2(1H)-one The title compound was prepared from 4-[2-(4-chlorophenyl)-4-(4-fluorophenyl)-1-hydroxy-1H-imidazol-5-yl]pyridin-2(1H)-one EXAMPLE 5, Step A) following the procedure described in EXAMPLE 2 (2.4 eq. of iodomethane was used).

Mass spectrum (LC-MS, ES+): 410.1 (M+1), LC 1: 3.19 min. $^1$H NMR (DMSO-d$_6$, 500 MHz): δ 8.08 (d, J=8.7 Hz, 2H); 7.78 (d, J=6.9 Hz, 1H); 7.62 (d, J=8.7 Hz, 2H); 7.58 (d, J=8.7 Hz, 1H); 7.57 (d, J=8.7 Hz, 1H); 7.22 (d, J=8.9 Hz, 1H); 7.20 (d, J=8.7 Hz, 1H); 6.56 (d, J=1.8 Hz, 1H); 6.22 (dd, J$_1$=6.9 Hz, J$_2$=1.8 Hz, 1H).

Step B: 2-(4-chlorophenyl)-9-fluoro-6-methyl-3,6-dihydro-7H-benzo[h]imidazo[4,5-f]isoquinolin-7-one The title compound was prepared from 4-[2-(4-chlorophenyl)-4-(4-fluorophenyl)-1-methoxy-1H-imidazol-5-yl]-1-methylpyridin-2(1H)-one of Step A following the procedure described in EXAMPLE 1, Step E.

Mass spectrum (LC-MS, ES+): 378.1 (M+1), LC 1: 2.24 min. $^1$H NMR (DMSO-d$_6$, 500 MHz): δ 10.06 (brd, 1H); 8.65 (d, J$_1$=8.7 Hz, J$_2$=6.4 Hz, 1H); 8.32 (d, J=8.2 Hz, 2H); 8.0 (brs, 1H); 7.70 (d, J=8.5 Hz, 2H); 7.63 (brs, 1H); 7.37 (d, J=7.1 Hz, 1H).

EXAMPLE 7

9-fluoro-2-(4-methoxyphenyl)-3,6-dihydro-7H-benzo[h]imidazo[4,5-f]isoquinolin-7-one

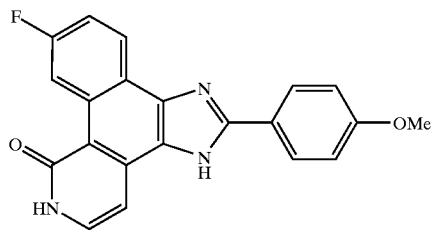

Step A: 4-[4-(4-fluorophenyl)-1-hydroxy-2-(4-methoxyphenyl)-1H-imidazol-5-yl]pyridin-2(1H)-one The title compound was prepared from 1-(4-fluorophenyl)-2-(2-fluoro-pyridin-4-yl)ethane-1,2-dione 2-oxime (EXAMPLE 1, Step B) following the procedure described in EXAMPLE 1, Step C (replacing trimethylacetaldehyde with 4-methoxybenzaldehyde).

Mass spectrum (LC-MS, ES+): 378.2 (M+1), LC 1: 1.34 min.

Step B: 9-fluoro-2-(4-methoxyphenyl)-3,6-dihydro-7H-benzo[h]imidazo[4,5-f]isoquinolin-7-one The title compound was prepared from 4-[4-(4-fluorophenyl)-1-hydroxy-2-(4-methoxyphenyl)-1H-imidazol-5-yl]pyridin-2(1H)-one of Step A following the procedure described in EXAMPLE 1, Step E.

Mass spectrum (LC-MS, ES+): 360.2 (M+1), LC 1: 1.55 min. $^1$H NMR (DMSO-d$_6$, 500 MHz): δ 11.7 (brs, 1H); 10.05 (brs, 1H); 8.63 (dd, J$_1$=8.9 Hz, J$_2$=6.4 Hz, 1H); 8.24 (brs, 2H); 7.60 (brd, 3H); 7.35 (d, J=6.9 Hz, 1H); 7.16 (d, J=8.7 Hz, 2H).

EXAMPLE 8

9-fluoro-2-methyl-3,6-dihydro-7H-benzo[h]imidazo[4,5-f]isoquinolin-7-one

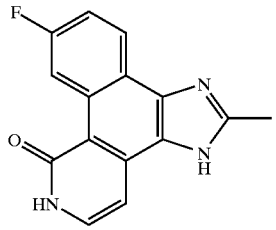

Step A: 4-[4-(4-fluorophenyl)-1-hydroxy-2-methyl-1H-imidazol-5-yl]pyridin-2(1H)-one The title compound was prepared from 1-(4-fluorophenyl)-2-(2-fluoro-pyridin-4-yl)ethane-1,2-dione 2-oxime EXAMPLE 1, Step B) following the procedure described in EXAMPLE 1, Step C (replacing trimethylacetaldehyde with 2-methyl-1,3-dioxolane).

Mass spectrum (LC-MS, ES+): 286.0 (M+1), LC 1: 0.86 min. $^1$H NMR (DMSO-d$_6$, 500 MHz): δ 7.45 (m, 2H); 7.31 (d, J=6.6 Hz, 1H); 7.23 (t, 1H); 7.18-7.10 (m, 2H); 6.38 (s, 1H); 6.02 (d, J=6.8 Hz, 1H).

Step B: 9-fluoro-2-methyl-3,6-dihydro-7H-benzo[h]imidazo[4,5-f]isoquinolin-7-one The title compound was prepared as a mixture of imidazole tautomers from 4-[4-(4-fluorophenyl)-1-hydroxy-2-methyl-1H-imidazol-5-yl]pyridin-2(1H)-one (EXAMPLE 8, Step A) following the procedure described in EXAMPLE 1, Step E.

Mass spectrum (LC-MS, ES+): 268.1 (M+1), LC 1: 1.44 min. $^1$H NMR (DMSO-d$_6$, 500 MHz) of the major tautomer: δ 13.25 (brd, 1H); 10.04 (brd, 1H); 8.50 (brs, 1H); 7.58 (brs, 2H); 7.22 (m, 1H); 6.65 (brs, 1H); 2.60 (s, 3H).

EXAMPLE 9

9-fluoro-2-(4-methylphenyl)-3,6-dihydro-7H-benzo[h]imidazo[4,5-f]isoquinolin-7-one

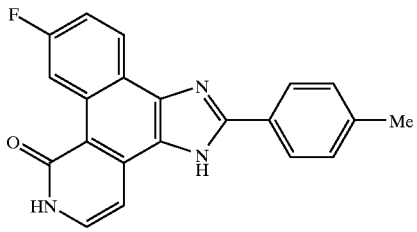

Step A: 4-[4-(4-fluorophenyl)-1-hydroxy-2-(4-methylphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 4-methylbenzaldehyde).

Mass spectrum (LC-MS, ES+): 362.1 (M+1), LC 1: 1.41 min. $^1$H NMR DMSO-d$_6$, 500 MHz): δ 7.96 (d, J=8.0 Hz, 2H); 7.56–7.12 (aromatic Hs, 7H); 6.45 (s, 1H); 6.09(d, J=7.1 Hz, 1H).

Step B: 9-fluoro-2-(4-methylphenyl)-3,6-dihydro-7H-benzo[h]imidazo[4,5-f]isoquinolin-7-one The title compound was prepared from 4-[4-(4-fluorophenyl)-1-hydroxy-2-(4-methylphenyl)-1H-imidazol-5-yl]pyridin-2(1H)-one of Step A following the procedure described in EXAMPLE 1, Step E.

Mass spectrum (LC-MS, ES+): 344.1 (M+1), LC 1: 1.70 min. $^1$H NMR (DMSO-d$_6$, 500 MHz) of the major tautomer: δ 11.7 (brs, 1H); 10.02 (dd, 1H); 8.63 (m, 1H); 8.18 (d, J=8.2 Hz, 2H); 7.658 (m, 2H); 7.41 (d, J=8.3 Hz, 2H); 7.34 (s, 1H); 2.40 (s, 3H).

EXAMPLE 10

2-(3-chlorophenyl)-9-fluoro-3,6-dihydro-7H-benzo[h]imidazo[4,5-f]isoquinolin-7-one

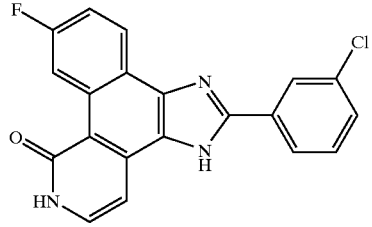

Step A: 4-[2-(3-chlorophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 3-chlorobenzaldehyde).

Mass spectrum (LC-MS, ES+): 382.2 (M+1), LC 1: 1.70 min.

Step B: 2-(3-chlorophenyl)-9-fluoro-3,6-dihydro-7H-benzo[h]imidazo[4,5-f]isoquinolin-7-one The title compound was prepared from 4-[2-(3-chlorophenyl)-4-(4-fluorophenyl)-1-hydroxy-1H-imidazol- 5-yl]pyridin-2(1H)-one of Step A following the procedure described in EXAMPLE 1, Step E.

Mass spectrum (LC-MS, ES+): 364.0 (M+1), LC 1: 2.12 min.

EXAMPLE 11

9-fluoro-2-(2-methylphenyl)-3,6-dihydro-7H-benzo[h]imidazo[4,5-f]isoquinolin-7-one

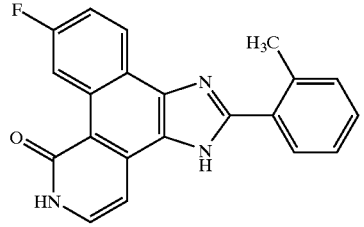

Step A: 4-[4-(4-fluorophenyl)-1-hydroxy-2-(2-methylphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-methylbenzaldehyde).

Mass spectrum (LC-MS, ES+): 362.1 (M+1), LC 1: 1.31 min.

Step B: 4-[4-(4-fluorophenyl)-2-(2-methylphenyl)-1H-imidazol-5-yl]pyridin-2(1H)-one The title compound was prepared from 4-[4-(4-fluorophenyl)-1-hydroxy-2-(2-methylphenyl)-1H-imidazol-5-yl]pyridin-2(1H)-one of Step A following the procedure described in EXAMPLE 1, Step D.

Mass spectrum (LC-MS, ES+): 346.1 (M+1), LC 1: 1.21 min.

Step C: 9-fluoro-2-(2-methylphenyl)-3,6-dihydro-7H-benzo[h]imidazo[4,5-f]isoquinolin-7-one The title compound was prepared from 4-[4-(4-fluorophenyl)-2-(2-methylphenyl)-1H-imidazol-5-yl]pyridin-2(1H)-one of Step B following the procedure described in EXAMPLE 1, Step E.

Mass spectrum (LC-MS, ES+): 344.1 (M+1), LC 1: 1.58 min.

EXAMPLE 12

2-(2,6-dimethoxyphenyl)-9-fluoro-3,6-dihydro-7H-benzo[h]imidazo[4,5-f]isoquinolin-7-one

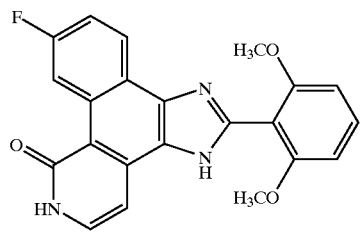

Step A: 4-[2-(2,6-dimethoxyphenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2,6-dimethoxybenzaldehyde).

Mass spectrum (LC-MS, ES+): 408.2 (M+1), LC 1: 1.24 min. $^1$H NMR (DMSO-$d_6$, 500 MHz): δ 11.6 (brs, 1H); 7.54-7.12 (aromatic Hs, 6H); 6.74 (d, J=8.5 Hz, 2H); 6.47 (s, 1H); 6.07 (d, J=6.8 Hz, 1H); 3.70 (s, 6H).

Step B: 2-(2,6-dimethoxyphenyl)-9-fluoro-3,6-dihydro-7H-benzo[h]imidazo[4,5-f]isoquinolin-7-one The title compound was prepared from 4-[2-(2,6-dimethoxyphenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 390.2 (M+1), LC 1: 2.01 min. $^1$H NMR (DMSO-$d_6$, 500 MHz) of the major tautomer: δ 13.40 (s, 1H); 11.64 (s, 1H); 10.08 (d, J=12.4 Hz, 1H); 8.38 (m, 1H); 7.55 (m, 3H); 7.25 (d, J=6.8 Hz, 1H); 6.47 (s, 1H); 6.84 (d, J=8.3 Hz, 2H); 3.71 (s, 6H).

EXAMPLE 13

9-fluoro-2-(2-methoxyphenyl)-3,6-dihydro-7H-benzo[h]imidazo[4,5-f]isoquinolin-7-one

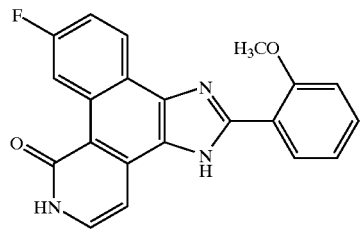

Step A: 4-[4-(4-fluorophenyl)-1-hydroxy-2-(2-methoxyphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-methoxybenzaldehyde).

Mass spectrum (LC-MS, ES+): 378.2 (M+1), LC 1: 1.74 min. Partial $^1$H NMR (DMSO-$d_6$, 500 MHz): δ 3.79 (s, 3H).

Step B: 9-fluoro-2-(2-methoxyphenyl)-3,6-dihydro-7H-benzo[h]imidazo[4,5-f]isoquinolin-7-one The title compound was prepared from 4-[4-(4-fluorophenyl)-1-hydroxy-2-(2-methoxyphenyl)-1H-imidazol-5-yl]pyridin-2(1H)-one of Step A following the procedure described in EXAMPLE 1, Step E.

Mass spectrum (LC-MS, ES+): 360.1 (M+1), LC 1: 1.62 min. $^1$H NMR (DMSO-$d_6$, 500 MHz) of the major tautomer: δ 12.98 (s, 1H); 11.75 (s, 1H); 10.08, (dd, $J_1$=14.4 Hz, $J_2$=2.5 Hz, 1H); 8.77 (dd, $J_1$=8.5 Hz, $J_2$=6.2 Hz, 1H); 7.60 (m, 3H); 7.27 (d, J=8.3 Hz, 2H); 7.16 (m, 1H); 4.00 (s, 3H).

EXAMPLE 14

2-(2-chlorophenyl)-9-fluoro-3,6-dihydro-7H-benzo[h]imidazo[4,5-f]isoquinolin-7-one

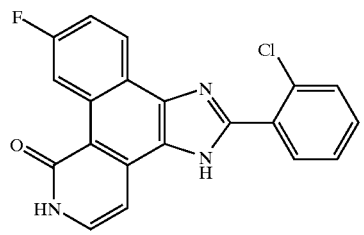

Step A: 2-(2-Chlorophenyl)-5-(4-fluorophenyl)-3-N-hydroxy-4-(pyridon-3-yl)-imidazole The title compound was prepared from 1-(4-fluorophenyl)-2-(2-fluoropyridin-4-yl)ethane-1,2-dione 2-oxime EXAMPLE 1, Step B) following the procedure described in EXAMPLE 1, Step C (replacing trimethylacetaldehyde with 2-chlorobenzaldehyde).

Mass spectrum (LC-MS, ES+): 382.2 (M+1), LC 1: 1.42 min.

Step B: 2-(2-chlorophenyl)-9-fluoro-3,6-dihydro-7H-benzo[h]imidazo[4,5-f]isoquinolin-7-one The title compound was prepared from 2-(2-chlorophenyl)-5-(4-fluoro-phenyl)-3-N-hydroxy-4-(pyridon-3-yl)-imidazole of Step A following the procedure described in EXAMPLE 1, Step E.

Mass spectrum (LC-MS, ES+): 364.1 (M+1), LC 1: 1.75 min. $^1$H NMR (DMSO-$d_6$, 500 MHz): δ 11.72 (brs, 1H); 10.06 (brd, J=11.9 Hz, 1H); 8.56 (brs, 1H); 7.89 (dd, $J_1$=7.6 Hz, $J_2$=1.7 Hz, 1H); 7.70 (d, J=7.3 Hz, 1H); 7.59 (m, 5H); 7.29 (brs, 1H).

EXAMPLE 15

9-fluoro-2-(2-fluorophenyl)-3,6-dihydro-7H-benzo[h]imidazo[4,5-f]isoquinolin-7-one

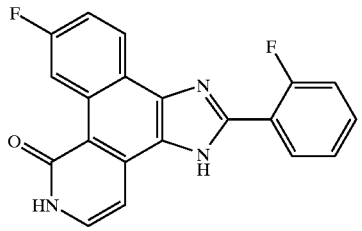

Step A: 4-[2-(2-fluorophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-fluorobenzaldehyde).

Mass spectrum (LC-MS, ES+): 350.2 (M+1).

Step B: 9-fluoro-2-(2-fluorophenyl)-3,6-dihydro-7H-benzo[h]imidazo[4,5-f]isoquinolin-7-one The title compound was prepared from 4-[2-(2-fluorophenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 348.0 (M+1), LC 1: 1.78 min. $^1$H NMR (DMSO-$d_6$, 500 MHz): δ 11.72 (brs, 1H); 10.06 (brs, 1H); 8.70 (brs, 1H); 8.17 (t, J=7.3 Hz, 1H); 7.60 (m, 2H); 7.52–7.20 (m, 3H); 6.65 (brs, 2H).

EXAMPLE 16

2-(2,6-dichlorophenyl)-9-fluoro-3,6-dihydro-7H-benzo[h]imidazo[4,5-f]isoquinolin-7-one

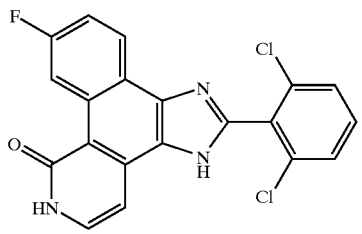

Step A: 4-[2-(2,6-dichlorophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2,6-dichlorobenzaldehyde).

Mass spectrum (LC-MS, ES+): 416.1 (M+1), LC 1: 1.62 min.

Step B: 2-(2,6-dichlorophenyl)-9-fluoro-3,6-dihydro-7H-benzo[h]imidazo[4,5-f]isoquinolin-7-one The title compound was prepared from 4-[2-(2,6-dichlorophenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 398.2 (M+1), LC 1: 1.86 min. $^1$H NMR (DMSO-$d_6$, 500 MHz) of the major tautomer: δ 11.72 (brs, 1H); 10.10 (brd, J=12.1 Hz, 1H); 8.58 (brs, 1H); 7.76–7.54 (m, 5H); 7.27 (brs, 1H).

EXAMPLE 17

2-(2,6-difluorophenyl)-9-fluoro-3,6-dihydro-7H-benzo[h]imidazo[4,5-f]isoquinolin-7-one

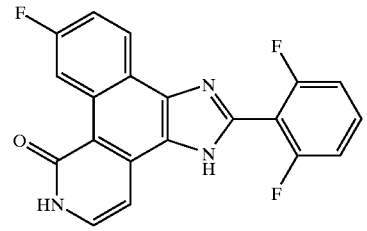

Step A: 4-[2-(2,6-difluorophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2,6-difluorobenzaldehyde).

Mass spectrum (LC-MS, ES+): 384.2 (M+1), LC 1: 1.48 min.

Step B: 2-(2,6-difluorophenyl)-9-fluoro-3,6-dihydro-7H-benzo[h]imidazo[4,5-f]isoquinolin-7-one The title compound was prepared from 4-[2-(2,6-difluorophenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 366.1 (M+1), LC 1: 1.72 min. $^1$H NMR (DMSO-$d_6$, 500 MHz) of the major tautomer: δ 11.72 (brs, 1H); 10.10 (brd, J=12.4 Hz, 1H); 8.50 (brs, 1H); 7.70 (m, 1H); 7.60 (brs, 3H); 7.39 (t, J=8.2 Hz, 2H); 7.30 (brs, 1H).

EXAMPLE 18

2-cyclohexyl-9-fluoro-3,6-dihydro-7H-benzo[h]imidazo[4,5-f]isoquinolin-7-one

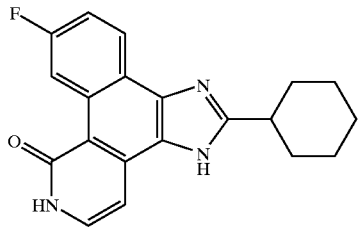

Step A: 4-[2-cyclohexyl-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with cyclohexanecarboxaldehyde).

Mass spectrum (LC-MS, ES+): 354.1 (M+1), LC 1: 1.31 min. $^1$H NMR (DMSO-$d_6$, 500 MHz): δ 11.50 (brs, 1H); 7.45 (m, 2H); 7.32 (brd, J=5.4 Hz, 1H); 7.14 (d, J=8.9 Hz, 1H); 7.12 (d, J=8.7 Hz, 1H); 6.39 (s, 1H); 6.01 (d, J=6.2 Hz, 1H); 2.82 (brs, 1H); 1.88 (m, 2H); 1.77 (m, 2H); 1.66 (m, 1H); 1.53 (m, 2H); 1.38–1.20 (m, 4H).

Step B: 2-cyclohexyl-9-fluoro-3,6-dihydro-7H-benzo[h]imidazo[4,5-f]isoquinolin-7-one The title compound was prepared from 4-[2-cyclohexyl-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 336.1 (M+1), LC 1: 1.44 min. $^1$H NMR (DMSO-$d_6$, 500 MHz): δ 13.08 (brs, 1H); 11.60 (brs, 1H); 10.00 (brs, 1H); 8.45 (brs, 1H); 7.55 (brs, 2H); 7.20 (brs, 1H); 2.98 (t, J=11.2 Hz, 1H); 2.10 (d, J=3.9 Hz, 1H); 1.85 (m, 2H); 1.72 (m, 3H); 1.50–1.16 (m, 4H).

EXAMPLE 19

2-(2-chloro-6-fluorophenyl)-9-fluoro-3,6-dihydro-7H-benzo[h]imidazo[4,5-f]isoquinolin-7-one

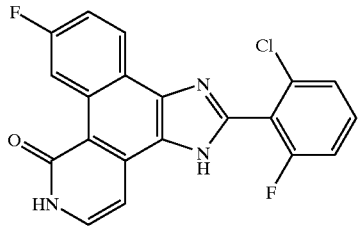

Step A: 4-[2-(2-chloro-6-fluorophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-chloro-6-fluorobenzaldehyde).

Mass spectrum (LC-MS, ES+): 400.2 (M+1), RT: 1.56 min.

Step B: 2-(2-chloro-6-fluorophenyl)-9-fluoro-3,6-dihydro-7H-benzo[h]imidazo[4,5-f]isoquinolin-7-one The title compound was prepared from 4-[2-(2-chloro-6-fluorophenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 382.1 (M+1), LC 1: 1.80 min.

EXAMPLE 20

2-(2-bromophenyl)-9-fluoro-3,6-dihydro-7H-benzo[h]imidazo[4,5-f]isoquinolin-7-one

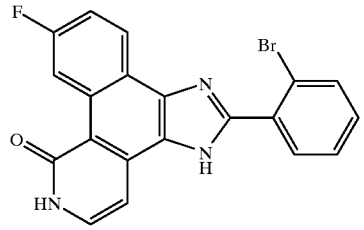

Step A: 4-[2-(2-bromophenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-bromobenzaldehyde).

Mass spectrum (LC-MS, ES+): 426.1 (M+1), LC 1: 1.45 min.

Step B: 2-(2-bromophenyl)-9-fluoro-3,6-dihydro-7H-benzo[h]imidazo[4,5-f]isoquinolin-7-one The title compound was prepared from 4-[2-(2-bromophenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 408.1 (M+1), LC 1: 1.76 min. $^1$H NMR (DMSO-$d_6$, 500 MHz): δ 11.72 (brs, 1H); 10.05 (brs, 1H); 8.52 (brs, 1H); 7.87 (dd, $J_1$=8.2 Hz, $J_2$=1.2 Hz, 1H); 7.81 (dd, $J_1$=7.8 Hz, $J_2$=1.1 Hz, 1H); 7.60 (dt, $J_1$=7.5 Hz, $J_2$=1.1 Hz, 4H); 7.51 (dt, $J_1$=7.5 Hz, $J_2$=1.6 Hz, 1H); 7.27 (brs, 1H).

EXAMPLE 21

9-fluoro-3,6-dihydro-7H-benzo[h]imidazo[4,5-f]isoquinolin-7-one

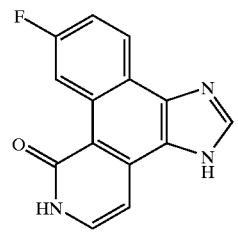

Step A: 4-[4-(4-fluorophenyl)-1-hydroxy-1H-imidazol-5-yl]pyridin-2(1H)-one

The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with formaldehyde).

Mass spectrum (LC-MS, ES+): 255.9 (M+1), LC 1: 0.75 min.

Step B: 9-fluoro-3,6-dihydro-7H-benzo[h]imidazo[4,5-f]isoquinolin-7-one

The title compound was prepared from 4-[4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 253.9 (M+1), LC 1: 1.09 min. $^1$H NMR (DMSO-$d_6$, 500 MHz): δ 11.70 (brs, 1H); 10.04 (d, J=13.0 Hz, 1H); 8.48 (brs, 1H); 8.44 (s, 1H); 7.58 (m, 2H); 7.24 (brs, 1H).

EXAMPLE 22

9-fluoro-2-(2-hydroxyphenyl)-3,6-dihydro-7H-benzo[h]imidazo[4,5-f]isoquinolin-7-one

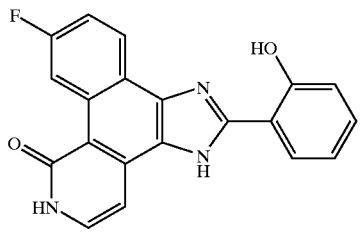

Step A: 4-[4-(4-fluorophenyl)-1-hydroxy-2-(2-hydroxyphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-hydroxybenzaldehyde).

Mass spectrum (LC-MS, ES+): 364.2 (M+1), LC 1: 1.86 min.

Step B: 9-fluoro-2-(2-hydroxyphenyl)-3,6-dihydro-7H-benzo[h]imidazo[4,5-f]isoquinolin-7-one The title compound was prepared from 4-[4-(4-fluorophenyl)-1-hydroxy-2-(2-hydroxyphenyl)-1H-imidazol-5-yl]pyridin-2(1H)-one of Step A following the procedure described in EXAMPLE 1, Step E. Mass spectrum (LC-MS, ES+): 346.1 (M+1), LC 1: 3.16 min. $^1$H NMR (DMSO-$d_6$, 500 MHz): δ 12.75 (brs, 1H); 11.8 (s, 1H); 10.06 (d, J=12.2 Hz, 1H); 8.66 (brs, 1H); 8.22 (d, J=6.8 z, 2H); 7.66 (brs, 2H); 7.41 (t, J=8.5 Hz, 1H); 7.29 (brs, 1H); 7.09 (m, 2H).

EXAMPLE 23

9-fluoro-2-(3-hydroxyphenyl)-3,6-dihydro-7H-benzo[h]imidazo[4,5-f]isoquinolin-7-one

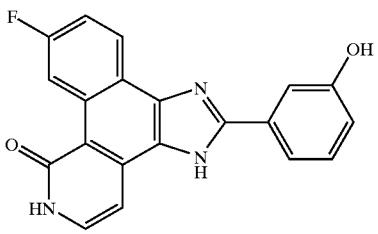

Step A: 4-[4-(4-fluorophenyl)-1-hydroxy-2-(3-hydroxyphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 3-hydroxybenzaldehyde).

Mass spectrum (LC-MS, ES+): 364.2 (M+1), LC 1: 1.53 min.

Step B: 9-fluoro-2-(3-hydroxyphenyl)-3,6-dihydro-7H-benzo[h]imidazo[4,5-f]isoquinolin-7-one The title compound was prepared from 4-[4-(4-fluorophenyl)-1-hydroxy-2-(3-hydroxyphenyl)-1H-imidazol-5-yl]pyridin-2(1H)-one of Step A following the procedure described in EXAMPLE 1, Step E.

Mass spectrum (LC-MS, ES+): 346.2 (M+1), LC 1: 1.94 min. $^1$H NMR (DMSO-$d_6$, 500 MHz): δ 11.7 (brs, 1H); 10.05 (brs, 1H); 9.8 (s, 1H); 8.63 (m, 1H); 7.72 (s, 2H); 7.60 (brs, 2H); 7.37 (t, J=8.5 Hz, 1H); 7.35 (brs, 1H); 6.92 (d, J=7.1 Hz, 1H).

EXAMPLE 24

9-fluoro-2-(4-hydroxyphenyl)-3,6-dihydro-7H-benzo[h]imidazo[4,5-f]isoquinolin-7-one

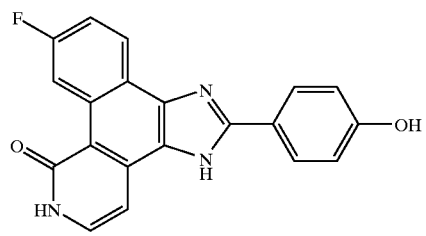

Step A: 4-[4-(4-fluorophenyl)-1-hydroxy-2-(4-hydroxyphenyl)-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 4-hydroxybenzaldehyde).

Step B: 9-fluoro-2-(4-hydroxyphenyl)-3,6-dihydro-7H-benzo[h]imidazo[4,5-f]isoquinolin-7-one The title compound was prepared from 4-[4-(4-fluorophenyl)-1-hydroxy-2-(4-hydroxyphenyl)-1H-imidazol-5-yl]pyridin-2(1H)-one of Step A following the procedure described in EXAMPLE 1, Step E.

Mass spectrum (LC-MS, ES+): 346.1 (M+1), LC 1: 1.346 min.

EXAMPLE 25

9-fluoro-2-[2-(trifluoromethyl)phenyl]-3,6-dihydro-7H-benzo[h]imidazo[4,5-f]isoquinolin-7-one

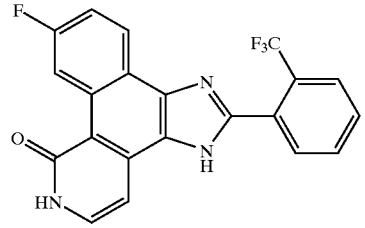

Step A: 4-{4-(4-fluorophenyl)-1-hydroxy-2-[2-(trifluoromethyl)phenyl]-1H-imidazol-5-yl}pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-trifluoromethylbenzaldehyde).

Mass spectrum (LC-MS, ES+): 416.15 (M+1), LC 1: 2.155 min.

Step B: 9-fluoro-2-[2-(trifluoromethyl)phenyl]-3,6-dihydro-7H-benzo[h]imidazo[4,5-f]isoquinolin-7-one The title compound was prepared from 4-{4-(4-fluorophenyl)-1-hydroxy-2-[2-(trifluoromethyl)phenyl]-1H-imidazol-5-yl}pyridin-2(1H)-one of Step A following the procedure described in EXAMPLE 1, Step E.

Mass spectrum (LC-MS, ES+): 398.05 (M+1), LC 1: 1.864 min. $^1$H NMR (DMSO-$d_6$, 500 MHz) of the major tautomer: δ 11.72 (brs, 1H); 10.09 (d, J=13.5 Hz, 1H); 8.47 (t, J=7.0 Hz, 1H); 8.00 (d, J=7.8 Hz, 1H); 7.95-7.54 (m, 6H); 7.28 (d, J=6.2 Hz, 1H).

EXAMPLE 26

2-(2-chloro-4-hydroxyphenyl)-9-fluoro-3,6-dihydro-7H-benzo[h]imidazo[4,5-f]isoquinolin-7-one

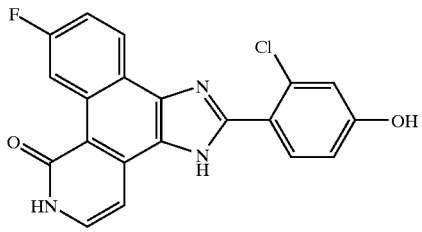

Step A: 4-[2-(2-chloro-4-hydroxyphenyl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 2-chloro-4-hydroxy-benzaldehyde).

Mass spectrum (LC-MS, ES+): 398.05 (M+1), LC 1: 1.264 min.

Step B: 2-(2-Chloro-4-hydroxy-phenyl)-9-fluoro-3,6-dihydro-7H-benz[h]imidazo[4,5-f]isoquinolin-7-one The title compound was prepared from 4-[2-(2-chloro-4-hydroxy-phenyl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 380 (M+1), LC 1: 1.876 min. $^1$H NMR (DMSO-$d_6$, 500 MHz): δ 11.7 (brs, 1H); 10.05 (brs, 1H); 8.55 (s, 1H); 7.70 (d, J=8.5 Hz, 1H); 7.59 (s, 2H); 7.28 (brs, 1H); 7.04 (d, J=2.3 Hz, 1H); 6.94 (dd, $J_1$=8.5 Hz, $J_2$=2.3 Hz, 1H).

EXAMPLE 27

2-cyclopentyl-9-fluoro-3,6-dihydro-7H-benzo[h]imidazo[4,5-f]isoquinolin-7-one

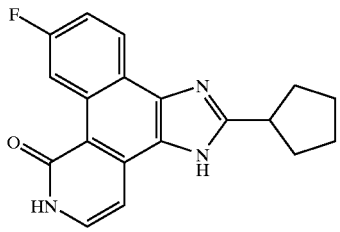

Step A: 4-[2-cyclopentyl-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with cyclopentyl methanal).

Mass spectrum (LC-MS, ES+): 340.1 (M+1), LC 1: 1.688 min.

Step B: 2-cyclopentyl-9-fluoro-3,6-dihydro-7H-benzo[h]imidazo[4,5-f]isoquinolin-7-one The title compound was prepared from 4-[2-cyclopentyl-4-(4-fluoro-phenyl)-1-hydroxy-1H-imidazol-5-yl]pyridin-2(1H)-one of Step A following the procedure described in EXAMPLE 1, Step E.

Mass spectrum (LC-MS, ES+): 322.1 (M+1), LC 1: 1.348 min. $^1$H NMR (DMSO-$d_6$, 500 MHz) of the major tautomer: δ 13.1 (s, 1H); 11.6 (brs, 1H); 10.05 (dd, $J_1$=14.0 Hz, $J_2$=2.5 Hz, 1H); 8.42 (dd, $J_1$=8.7 Hz, $J_2$=6.1 Hz, 1H); 7.50 (m, 2H); 7.24 (d, J=6.6 Hz, 1H); 3.40 (m, 1H); 2.14 (m, 2H); 2.00 (m, 2H); 1.82 (m, 2H); 1.70 (m, 2H).

EXAMPLE 28

2-(Propyl)-9-fluoro-3,6-dihydro-7H-benz[h]imidazo[4,5-f]isoquinolin-7-one

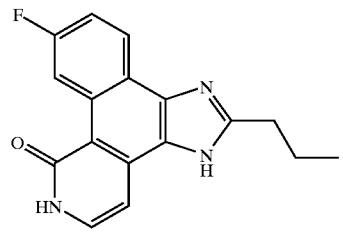

Step A: 4-[4-(4-fluorophenyl)-1-hydroxy-2-propyl-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with butyraldehyde).

Mass spectrum (LC-MS, ES+): 314.15 (M+1), LC 1: 1.081 min.

Step B: 2-(Propyl)-9-fluoro-3,6-dihydro-7H-benz[h]imidazo[4,5-f]isoquinolin-7-one The title compound was prepared from 4-[4-(4-fluorophenyl)-1-hydroxy-2-propyl-1H-imidazol-5-yl]pyridin-2(1H)-one of Step A following the procedure described in EXAMPLE 1, Step E.

Mass spectrum (LC-MS, ES+): 296.15 (M+1), LC 1: 1.238 min. $^1$H NMR (DMSO-$d_6$, 500 MHz) of the major tautomer: δ 13.2 (s, 1H); 11.6 (brs, 1H); 10.05 (d, J=14.2 Hz); 8.37 (m, 1H); 7.52 (m, 2H); 7.23 (d, J=6.7 Hz, 1H); 2.92 (m, 2H); 1.87 (m, 2H); 0.99 (t, J=7.3 Hz, 3H).

EXAMPLE 29

2-(3-chlorothien-2-yl)-9-fluoro-3,6-dihydro-7H-benzo[h]imidazo[4,5-f]isoquinolin-7-one

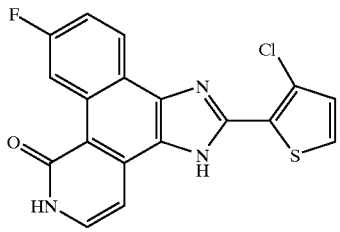

Step A: 4-[2-(3-chlorothien-2-yl)-4-(4-fluorophenyl)-1-hydroxy-1H-imidazol-5-yl]pyridin-2(1H)-one The title compound was prepared from 1-(4-fluorophenyl)-2-(2-fluoropyridin-4-yl)ethane-1,2-dione 2-oxime (EXAMPLE 1, Step B) following the procedure described in EXAMPLE 1, Step C (replacing trimethylacetaldehyde with 3-chlorothiophene-2-carbaldehyde).

Mass spectrum (LC-MS, ES+): 387.95 (M+1), LC 1: 1.592 min.

Step B: 2-(3-chlorothien-2-yl)-9-fluoro-3,6-dihydro-7H-benzo[h]imidazo[4,5-f]isoquinolin-7-one The title compound was prepared from 4-[2-(3-chlorothien-2-yl)-4-(4-fluorophenyl)-1-hydroxy-1H-imidazol-5-yl]pyridin-2(1H)-one of Step A following the procedure described in EXAMPLE 1, Step E.

Mass spectrum (LC-MS, ES+): 369.95 (M+1), LC 1: 2.048 min.

EXAMPLE 30

9-fluoro-2-pyridin-3-yl-3,6-dihydro-7H-benzo[h]imidazo[4,5-f]isoquinolin-7-one

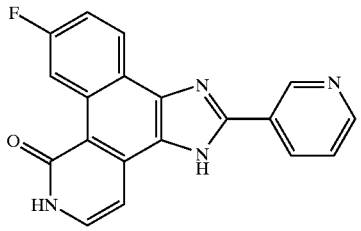

Step A: 4-[4-(4-fluorophenyl)-1-hydroxy-2-pyridin-3-yl-1H-imidazol-5-yl]pyridin-2(1H)-one The title compound was prepared from 1-(4-fluorophenyl)-2-(2-fluoropyridin-4-yl)ethane-1,2-dione 2-oxime EXAMPLE 1, Step B) following the procedure described in EXAMPLE 1, Step C (replacing trimethylacetaldehyde with 3-pyridinecarboxaldehyde).

Mass spectrum (LC-MS, ES+): 349.1 (M+1), LC 1: 1.13 min.

Step B: 9-fluoro-2-pyridin-3-yl-3,6-dihydro-7H-benzo[h]imidazo[4,5-f]isoquinolin-7-one The title compound was prepared from 4-[4-(4-fluorophenyl)-1-hydroxy-2-pyridin-3-yl-1H-imidazol-5-yl]pyridin-2(1H)-one of Step A following the procedure described in EXAMPLE 1, Step E.

Mass spectrum (LC-MS, ES+): 331.1 (M+1), LC 1: 1.29 min. $^1$H NMR (DMSO-$d_6$, 500 MHz): δ 11.75 (brs, 1H); 11.05 (d, J=13.8 Hz, 1H); 9.46 (s, 1H); 8.69 (d, J=3.9 Hz, 1H); 8.60 (m, 2H); 7.63 (m, 3H); 7.35 (d, J=6.9 Hz, 1H).

EXAMPLE 31

9-Fluoro-1-methyl-2-phenyl-1,6-dihydro-7H-benz[h]imidazo[4,5-f]isoquinolin-7-one

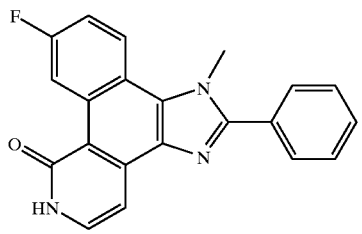

Step A: 4-[5-(4-fluorophenyl)-1-methyl-3-oxido-2-phenyl-1H-imidazol-4-yl]pyridin-2(1H)-one To a suspension of 1-(4-fluorophenyl)-2-(2-fluoropyridin-4-yl)ethane-1,2-dione 2-oxime (Example 1, Step B) (400 mg, 1.52 mmol) in acetic acid (7.6 mL) was added benzaldehyde (170 μL, 1.68 mmol) followed by methylamine (144 μL, 40 wt. % in H$_2$O, 1.68 mmol), and the mixture was heated for 41 hours at 100° C. It was cooled and acetic acid was removed in vacuo. The residue was taken up in H$_2$O and was concentrated in vacuo two times. This was repeated with toluene to obtain crude residue. The crude residue was dissolved in a mixture of CH$_2$Cl$_2$/MeOH, filtered off solid (unreacted, hydrolyzed imidazole), and the solvent was removed in vacuo. The crude product was pre-absorbed on silica gel and purified by flash chromatography eluting with 5% MeOH/CH$_2$Cl$_2$ followed by 10% 2M NH$_3$ in MeOH/CH$_2$Cl$_2$ to obtain 270 mg of the title compound.

$^1$H NMR (DMSO-$d_6$, 500 MHz): δ 7.89 (d, J=8.3 Hz, 2H); 7.60–7.52 (aromatic H's, 5H); 7.40 (t, J=8.9 Hz, 2H); 7.23 (d, J=6.9 Hz, 1H); 6.72 (d, J=1.2 Hz, 1H); 6.22 (dd, J$_1$=7.0 Hz, J$_2$=1.7 Hz, 1H); 3.39 (s, 3H). MS(ES) 362 (M+1); LC 1: 1.33 min.

Step B: 4-[5-(4-fluorophenyl)-1-methyl-2-phenyl-1H-imidazol-4-yl]pyridin-2(1H)-one To a solution of 4-[5-(4-fluorophenyl)-1-methyl-3-oxido-2-phenyl-1H-imidazol-4-yl]pyridin-2(1H)-one of Step A (56 mg, 0.155 mmol) in CHCl$_3$ (2 mL) was added phosphorous trichloride (16 μL, 0.186 mmol) dropwise at room temperature. The reaction mixture was heated at 60° C. for 2 hours, cooled, and poured into 1N NaOH/ice solution. The aqueous layer was extracted with CH$_2$Cl$_2$, and the combined organic extracts were washed with H$_2$O followed by brine. After drying over Na$_2$SO$_4$, the solvent was removed in vacuo. The crude material was purified by preparative thin layer chromatography (1:10 MeOH:CH$_2$Cl$_2$ as an eluent) to obtain 21.8 mg of the title compound.

$^1$H NMR (DMSO-$d_6$, 500 MHZ): δ 11.26 (s, NH); 7.75 (d, J=7.1 Hz, 2H); 7.50 (m, 5H); 7.42 (t, J=8.9 Hz, 2H); 7.20 (d, J=7.3 Hz, 1H); 6.26 (m, 2H); 3.42 (s, 3H). MS(ES) 346.1 (M+1); LC 1: 1.38 min.

Step C: 9-Fluoro-1-methyl-2-phenyl-1,6-dihydro-7H-benz[h]imidazo[4,5-f]isoquinolin-7-one The title compound was prepared from 4-[5-(4-fluorophenyl)-1-methyl-2-phenyl-1H-imidazol-4-yl]pyridin-2(1H)-one of Step B according to the procedure described in EXAMPLE 1, Step E.

$^1$H NMR (DMSO-$d_6$, 500 MHZ): δ 11.73 (brs, NH); 10.26 (dd, J$_1$=14 Hz, J$_2$=2.8 Hz, 1H); 8.68 (dd, J$_1$=9.1 Hz, J$_2$=6.1 Hz, 1H); 7.85 (d, J=6.4 Hz, 2H); 7.61 (m, 5H); 7.36 (d, J=6.8 Hz, 1H); 4.27 (s, 3H). MS(ES) 344.1 (M+1); LC 1: 1.73 min.

EXAMPLE 32

1-ethyl-9-fluoro-2-phenyl-1,6-dihydro-7H-benzo[h]imidazo[4,5-f]isoquinolin-7-one

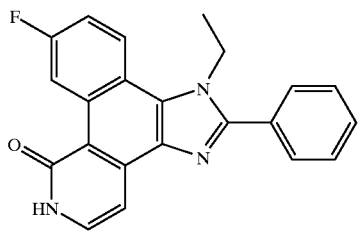

The title compound was prepared from ethylamine (70 wt. % in H$_2$O) according to the procedures described in EXAMPLE 31.

$^1$H NMR (DMSO-d$_6$, 500 MHZ): δ 11.74 (brs, NH); 10.30 (dd, J$_1$=14 Hz, J$_2$=2.5 Hz, 1H); 8.53 (dd, J$_1$=9.0 Hz, J$_2$=6.0 Hz, 1H); 7.77 (d, J=6.5 Hz, 2H); 7.62 (m, 5H); 7.35 (d, J=6.6 Hz, 1H); 4.66 (q, J=7.1 Hz, 3H); 1.44 (t, J=7.1 Hz). MS(ES) 358.1 (M+1); LC 1: 1.86 min.

EXAMPLE 33

1-benzyl-9-fluoro-2-phenyl-1,6-dihydro-7H-benzo[h]imidazo[4,5-f]isoquinolin-7-one

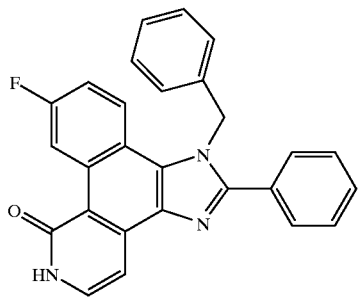

The title compound was prepared from benzylamine according to the procedures described in EXAMPLE 31.

$^1$H NMR (DMSO-d$_6$, 500 MHZ): δ 11.78 (brs, NH); 10.23 (dd, J$_1$=14 Hz, J$_2$=2.6 Hz, 1H); 8.16 (dd, J$_1$=9.0 Hz, J$_2$=6.3 Hz, 1H); 7.71-7.25 (11 aromatic H's); 7.09 (d, J=7.7 Hz, 1H); 5.94 (s, 2H). MS(ES) 420.1 (M+1); LC 1: 2.32 min.

EXAMPLE 34

1-[2-(dimethylamino)ethyl]-9-fluoro-2-phenyl-1,6-dihydro-7H-benzo[h]imidazo[4,5-f]isoquinolin-7-one

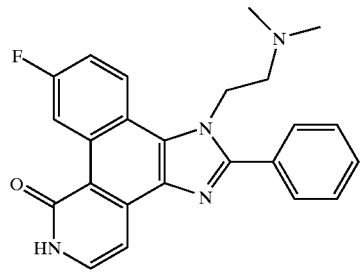

The title compound was prepared from N,N-dimethylethylenedianine according to the procedures described in EXAMPLE 31.

$^1$H NMR (CDCl$_3$, 500 MHZ): δ 10.21 (d, J=13.5 Hz, 1H); 8.32 (dd, J$_1$=9.0 Hz, J$_2$=6.0 Hz, 1H); 7.69 (m, 2H); 7.55 (m, 4H); 7.45 (m, 2H); 4.66 (m, 2H); 2.74 (m, 2H); 2.12 (s, 6H). MS(ES) 401.2 (M+1); LC 1: 1.22 min.

EXAMPLE 35

1-cyclopropyl-9-fluoro-2-phenyl-1,6-dihydro-7H-benzo[h]imidazo[4,5-f]isoquinolin-7-one

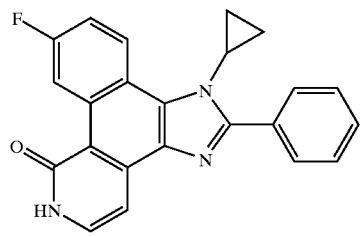

The title compound was prepared from cyclopropylamine according to the procedures described in EXAMPLE 31.

$^1$H NMR (DMSO-d$_6$, 500 MHZ): δ 11.73 (brs, NH); 10.23 (dd, J$_1$=14.1 Hz, J$_2$=2.6 Hz, 1H); 9.04 (dd, J$_1$=9.0 Hz, J$_2$=6.2 Hz, 1H); 8.03 (d, J=6.9 Hz, 2H); 7.6 (5 aromatic H's); 7.36 (d, J=6.8 Hz, 1H); 4.32 (m, 1H); 1.26 (m, 2H); 0.6 (m, 2H). MS(ES) 370.1 (M+1); LC 1: 1.97 min.

EXAMPLE 36

9-fluoro-1-methyl-2-(2-methylphenyl)-1,6-dihydro-7H-benzo[h]imidazo[4,5-f]isoquinolin-7-one

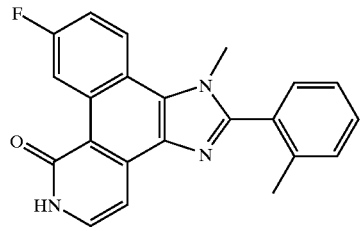

The title compound was prepared from methylamine (40 wt. % in H$_2$O) and 2-methylbenzaldehyde according to the procedures described in EXAMPLE 31.

¹H NMR (DMSO-d₆, 500 MHZ): δ 11.72 (brs, NH); 10.27 (dd, J₁=14.2 Hz, J₂=2.8 Hz, 1H); 8.67 (dd, J₁=9.1 Hz, J₂=6.3 Hz, 1H); 7.63-7.33 (7 aromatic H's); 4.06 (s, 3H); 2.22 (s, 3H). MS(ES) 358.1 (M+1); LC 1: 1.80 min.

EXAMPLE 37

2-(2,6-dichlorophenyl)-9-fluoro-1-methyl-1,6-dihydro-7H-benzo[h]imidazo[4,5-f]isoquinolin-7-one

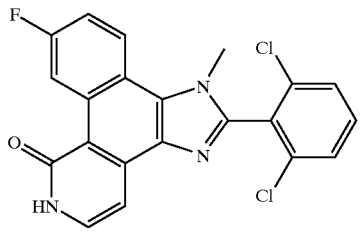

The title compound was prepared from methylamine (40 wt. % in H₂O) and 2,6-dichlorobenzaldehyde according to the procedures described in EXAMPLE 31.

¹H NMR (DMSO-d₆, 500 MHZ): δ 11.78 (brs, NH); 10.28 (dd, J₁=14.0 Hz, J₂=2.8 Hz, 1H); 8.69 (dd, J₁=9.2 Hz, J₂=6.2 Hz, 1H); 7.78-7.59 (5 aromatic H's); 7.31 (d, J=6.9 Hz, 1H); 4.07 (s, 3H). MS(ES) 412.0 (M+1); LC 1: 2.85 min.

EXAMPLE 38

2-tert-butyl-9,10-dichloro-3,6-dihydro-7H-benzo[h]imidazo[4,5-f]isoquinolin-7-one (isomer A) and 2-tert-butyl-8,9-dichloro-3,6-dihydro-7H-benzo[h]imidazo[4,5-f]isoquinolin-7-one (isomer B)

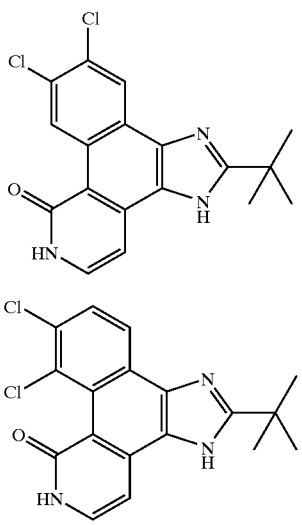

Step A: N-Methoxy-N-methyl-3,4-dichlorobenzamide

To a suspension of 3,4-dichlorobenzoic acid (1.0 g, 5.24 mmol) in CH₂Cl₂ (25 mL) was added N,O-dimethylhydroxylamine hydrochloride (613 mg, 6.28 mmol) followed by N-methylmorpholine (865 μL, 7.85 mmol) and 1-(3-dimethylaminopropyl)-3-ethylcarbodiimide hydrochloride (1.2 g, 6.28 mmol) at which point the reaction mixture became homogeneous. After 2 h, the reaction mixture was diluted with EtOAc and washed with 1N HCl, H₂O, saturated NaHCO₃ solution and brine, sequentially. The organic layer was dried over Na₂SO₄, and the removal of solvent in vacuo gave the title compound (1.16 g) that required no further purification.

¹H NMR (CDCl₃, 500 MHZ): δ 7.82 (d, J=1.8 Hz, 1H); 7.56 (dd, J₁=6.4 Hz, J₂=2.0 Hz, 1H); 7.48 (d, J=8.4 Hz, 1H); 3.54 (s, 3H); 3.36 (s, 3H).

Step B: 1-(3,4-dichlorophenyl)-2-(2-fluoropyridin-4-yl)ethanone

The title compound was prepared from N-methoxy-N-methyl-3,4-dichlorobenzamide of Step A according to the procedure described in EXAMPLE 1, Step A.

¹H NMR (CDCl₃, 500 MHZ): δ 8.20 (d, J=5.1 Hz, 1H); 8.07 (d, J=2.1 Hz, 1H); 7.81 (dd, J₁=8.5 Hz, J₂=2.1 Hz, 1H); 7.59 (d, J=8.4 Hz, 1H); 6.84 (s, 1H); 4.29 (s, 2H). MS(ES) 283.9 (M+1); LC 1: 2.52 min.

Step C: 1-(3,4-dichlorophenyl)-2-(2-fluoropyridin-4-yl)ethane-1,2-dione 2-oxime

The title compound was prepared from 1-(3,4-dichlorophenyl)-2-(2-fluoropyridin-4-yl)ethanone of Step B according to the procedure described in EXAMPLE 1, Step B as a mixture of cis and trans isomers.

¹H NMR (DMSO-d₆, 500 MHZ) of major isomer: δ 13.31 (brs, 1H); 8.35 (d, J=5.1 Hz, 1H); 8.17 (d, J=2.0 Hz, 1H); 7.83 (m, 2H); 7.42 (m, 1H); 7.30 (s, 1H). MS(ES) 313.1 (M+1); LC 1: 3.15 and 3.20 min.

Step D: 4-[2-tert-butyl-4-(3,4-dichlorophenyl)-1-hydroxy-1H-imidazol-5-yl]pyridin-2(1H)-one The title compound was prepared according to the procedure described in EXAMPLE 1, Step C from 1-(3,4-dichlorophenyl)-2-(2-fluoropyridin-4-yl)ethane-1,2-dione 2-oxime of Step C.

¹H NMR (CDCl₃, 500 MHZ): δ 7.56 (d, J=1.8 Hz, 1H); 7.29 (d, J=8.2 Hz, 1H); 7.21 (dd, J₁=8.2 Hz, J₂=1.8 Hz, 1H); 7.15 (d, J=6.8 Hz, 1H); 6.63 (d, J=1.1 Hz, 1H); 6.14 (dd, J₁=6.9 Hz, J₂=1.6 Hz, 1H); 1.42 (s, 9H).

Step E: 2-tert-butyl-9,10-dichloro-3,6-dihydro-7H-benzo[h]imidazo[4,5-f]isoquinolin-7-one (isomer A) and 2-tert-butyl-8,9-dichloro-3,6-dihydro-7H-benzo[h]imidazo[4,5-f]isoquinolin-7-one (isomer B)

The title compounds were prepared as regioisomers according to the procedure described in EXAMPLE 1, Step E from 4-[2-tert-butyl-4-(3,4-dichloro-phenyl)-1-hydroxy-1H-imidazol-5-yl]pyridin-2(1H)-one of Step D.

¹H NMR (DMSO-d₆, 500 MHz) of the major tautomer of A: δ 12.98 (s, 1H); 11.75 (brd, J=6.2 Hz, 1H); 10.55 (s, 1H); 8.84 (s, 1H); 7.56 (m, 1H); 7.27 (d, J=6.7 Hz, 1H); 1.5 (s, 9H). MS(ES) 360.2 (M+1); LC 1: 2.48 min.

¹H NMR (DMSO-d₆, 500 MHz) of B: δ 11.57 (brd, J=4.8 Hz, 1H); 8.45 (d, J=8.7 Hz, 1H); 7.86 (d, J=8.5 Hz, 1H); 7.60 (d, J=6.4 Hz, 1H); 7.16 (d, J=6.6 Hz, 1H); 1.5 (s, 9H). MS(ES) 360.1 (M+1); LC 1: 2.13 min.

EXAMPLE 39

9,10-dichloro-2-(2,6-dichlorophenyl)-3,6-dihydro-7H-benzo[h]imidazo[4,5-f]isoquinolin-7-one (isomer A) and 8,9-dichloro-2-(2,6-dichlorophenyl)-3,6-dihydro-7H-benzo[h]imidazo[4,5-f]isoquinolin-7-one (isomer B)

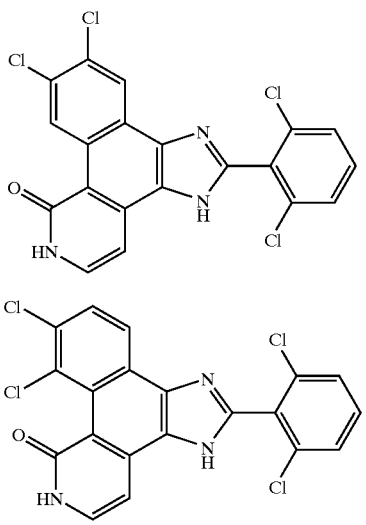

A

B

The title compounds were prepared according to the procedures described in EXAMPLE 38 using 2,6-dichlorobenzaldehyde in Step D.

¹H NMR (DMSO-d₆, 500 MHz) of the major tautomer of A: δ 11.89 (brd, J=4.2 Hz, 1H); 10.61 (s, 1H); 8.61 (s, 1H); 7.78–7.62 (m, 4H); 7.30 (d, J=6.6 Hz, 1H). MS(ES) 450 (M+1); LC 1: 3.0 min.

¹H NMR (DMSO-d₆, 500 MHz) of the major tautomer of B: δ 11.62 (brs, 1H); 8.23 (d, J=8.3 Hz, 1H); 7.91 (d, J=8.9 Hz, 1H); 7.76–7.60 (m, 4H); 7.11 (d, J=6.7 Hz, 1H). MS(ES) 450 (M+1); LC 1: 2.6 min.

EXAMPLE 40

2-tert-butyl-3,6-dihydro-7H-benzo[h]imidazo[4,5-f]isoquinolin-7-one

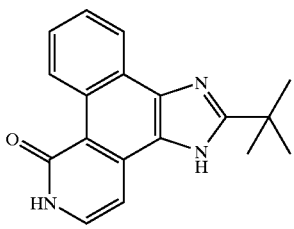

The title compound was prepared according to the procedures described in EXAMPLE 38 from benzoic acid.

¹H NMR (DMSO-d₆, 500 MHz) of the major tautomer: δ 12.82 (s, 1H); 11.50 (brs, 1H); 10.25 (d, J=8.7 Hz, 1H); 8.51 (d, J=8.9 Hz, 1H); 7.68–7.47 (m, 3H); 7.26 (d, J=6.6 Hz, 1H); 1.51 (s, 9H). MS(ES) 292.2 (M+1); LC 1: 1.79 min.

EXAMPLE 41

3-methyl-2-piperidin-4-yl-10-(trifluoromethyl)-3,6-dihydro-7H-benzo[h]imidazo[4,5-f]isoquinolin-7-one

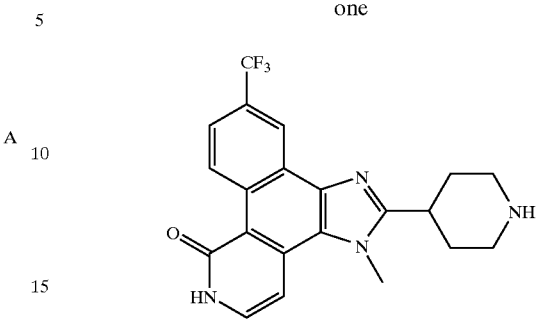

Step A: N-benzyloxycarbonyl piperidine-4-carboxylic acid

To a cooled (0° C.) and stirred solution of piperidine-4-carboxylic acid (68.64 g, 0.53 mol) in water (100 mL) and TMF (200 mL) containing sodium hydroxide (23.4 g, 0.58 mol) were added dropwise, simultaneously, benzyl chloroformate (10 g, 0.58 mol) and a solution of sodium hydroxide (23.4, 0.58 mol) in 100 mL water, over 20 min. The reaction mixture was then stirred for 30 min and diluted with ethyl acetate (250 mL), shaken and the organic layer discarded. The pH of the aqueous phase was adjusted to 1 with 3M HCl and extracted with methylene chloride (3×200 mL). The combined extracts were dried over sodium sulfate and the solvent evaporated in vacuo. Ether (50 mL) and hexane (50 mL) were added and the solvent slowly evaporated in vacuo giving a solid which was triturated with 20% ether/hexane and filtered to afford a white solid 136.5 g 98%.

M.P. 73–74° C. NMR (300 MHz, CDCl₃) δ: 7.2–7.4 (m, 5H); 5.12 (s, 2H); 4.09 (brd, 2H); 2.96 (brt, 2H); 2.52 (m, 1H); 1.93 (m, 2H); 1.69 (m, 2H).

Step B: N-methyl-N-methoxy 1-benzyloxycarbonylpiperidin-4-carboxamide.

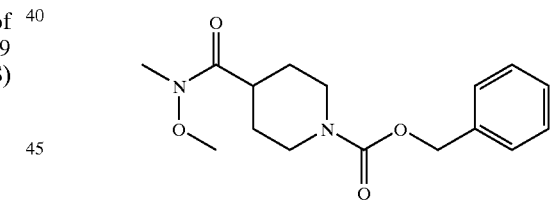

To a stirred and cooled (−5° C.) solution of N-benzyloxycarbonyl 4-piperidinecarboxylic acid (133.4 g, 0.51 mol) in methylene chloride (1000 mL) was added DMF (0.5 mL, catalytic), followed by dropwise addition of oxalyl chloride (50 mL, 0.57 mol) over 30 min. The reaction mixture was then allowed to warm to room temperature over 3 h, the volatiles evaporated in vacuo and the residue azeotroped with methylene chloride (2×). The crude acid chloride thus obtained was dissolved in methylene chloride (1300 mL) and the solution cooled to 0° C. before addition of N,O-dimethylhydroxylamine hydrochloride (59.7 g, 0.61 mol). Triethylamine (180 mL, 1.29 mol) was added dropwise over 1 h, and the reaction allowed to warm to room temperature over 2 h. The mixture was poured into 10% citric acid solution (750 mL) and ether (2000 mL) and the phases separated. The organic phase was washed with water, saturated aqueous NaHCO₃ and brine, the aqueous phases back extracted with ether and the combined organic extracts dried over sodium sulfate and the solvent evaporated in vacuo. The product was obtained as a pale yellow oil, yield 157.5 g (quantitative yield). The material obtained was used without further purification in the next step.

Step C: N-benzyloxycarbonyl piperidin-4-carboxaldehyde.

N-Methyl-N-methoxy 1-benzyloxycarbonylpiperidin-4-carboxamide (79.9 g, 261 mmol) was azeotroped with toluene (2×200 mL) to remove any water and dissolved in THF (700 mL). The solution was cooled to −60° C., before dropwise addition of a solution of lithium aluminum hydride in TBF (1 M, 100 mL, 100 mmol). The temperature of the reaction mixture was allowed to rise slowly to −30° C. over approx. 1 h. The mixture was transferred by cannula into a rapidly stirred mixture of ethyl acetate (200 mL) and 10% aqueous citric acid (500 mL), cooled to 0° C. After addition was complete, ether (500 mL) was added and the phases separated. The organic layer was washed with 1M HCl, water, saturated sodium bicarbonate solution and brine. After drying over anhydrous sodium sulfate, the solvent was evaporated in vacuo to afford the crude product, used without further purification (59 g).

NMR (300 MHz, CDCl$_3$) δ: 9.66 (s, 1H); 7.2–7.4 (m, 5H); 5.13 (s, 2H); 4.0-4.15 (m, 2H); 3.0 (m, 2H); 2.4 (m, 1H); 1.9 (m, 2H); 1.6 (m, 2H).

Step D: N-methyl-N-methoxy (3-trifluoromethyl) phenylcarboxamide.

To a suspension of N,O-dimethylhydroxylamine hydrochloride (58.2 g, 0.60 mol) in dichloromethane (1 L) at 0° C., under argon, was added 3-trifluoro-methylbenzoyl chloride (104.0 g, 0.50 mol) followed by a slow addition (≦+5° C.) of triethylamine (152.3 mL, 1.09 mol). The reaction was aged for 30 min. at +5° C. and then allowed to warm to room temperature. TLC (1:1, ethyl acetate/hexane) showed the reaction to be complete. The reaction was then washed with 5% aqueous citric acid (500 mL) and 5% aqueous sodium bicarbonate. The aqueous extracts were back extracted with methylene chloride (100 mL) and the combined methylene chloride extracts dried over sodium sulfate, filtered and concentrated to an oil. The oil was redissolved in toluene (2×100 mL) and evaporated in vacuo to afford the title amide (114.7 g, 98%).

NMR (300 MHz, CDCl$_3$) δ: 7.98 (s, 1H); 7.89 (d, J=7.8 Hz, 1H); 7.72 (d, J=7.8 Hz, 1H); 7.55 (t, J=7.8 Hz, 1H); 3.55 (s, 3H); 3.39 (s, 3H).

Step E: 2-(2-fluoropyridin-4-yl)-1-[3-(trifluoromethyl) phenyl]ethanone.

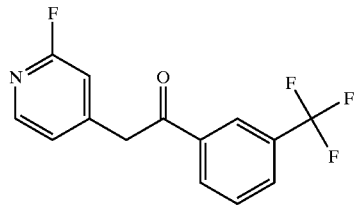

To a stirring solution of diisopropylamine (17.69 mL, 0.135 mol) in anhydrous THP (200 mL) at −78° C., under argon, was added n-butyllithium (54.0 mL, 2.5M in hexane, 0.135 mol), followed after 5 min. by a solution of 2-fluoro-4-methyl-pyridine (10 g, 0.090 mol) in anhydrous THF (20 mL). After stirring for 15 min. at −78° C., a solution of N-methoxy-N-methyl-3-trifluoromethylbenzamide (23.08 g, 0.099 mol) in anhydrous THF (10 mL) was added to the reaction mixture which was then stirred for 5 min., and allowed to warm to 0° C. The reaction was quenched with water (400 mL), and extracted with ethyl acetate (3×200 mL). The ethyl acetate extracts were combined, dried over anhydrous sodium sulfate, filtered, and concentrated to an oil which was chromatographed on silica gel (1 kg), eluting with 20% ethyl acetate in hexane to give 21.6 g (85%) of the title compound.

$^1$H NMR (300 MHz, CDCl$_3$) δ: 8.25(1H, s); 8.20(1H, d, J 5.1 Hz); 8.18(1H, d, J 9.3 Hz); 7.88(1H, d, J 7.8 Hz); 7.67(1H, t, J 7.8 Hz); 7.09(1H, d, J 5.1 Hz); 6.86(1H, s); 4.37(2H, s).

Step F: 1-(2-fluoropyridin-4-yl)-2-[3-(trifluoromethyl) phenyl]ethane-1,2-dione 1-oxime.

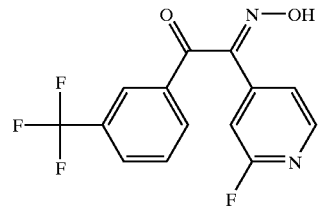

To a mixture of 2-(2-fluoropyridin-4-yl)-1-[3-(trifluoromethyl)-phenyl]ethanone (10.80 g, 0.038 mol) in ethanol (200 mL), at −10° C., under argon, was added tert-butylnitrite (5.0 mL, 0.042 mol) and hydrochloric acid (12.2 mL, 2.5M in ethanol, 0.031 mol) dropwise while maintaining the temperature below −5° C. Upon completion of additions, the reaction was allowed to warm to RT for 2 h. The reaction was concentrated iii vacuo, diluted with water (100 mL), basified with saturated sodium bicarbonate (200 ml). This mixture was then extracted with ethyl acetate (3×400 mL). The organic layers were combined, washed with water (300 mL), dried with brine (300 mL) and anhydrous sodium sulfate, filtered and concentrated to an oil which weighed 11.4 g (96%).

$^1$H NMR (300 MHz, CDCl$_3$) δ: 8.31 (1H, s); 8.29 (1H, d, J 5.3 Hz); 8.24 (1H, d, J 7.8 Hz); 7.92 (1H, d, J 8.1 Hz); 7.71 (1H, t, J 7.8 Hz); 7.40 (1H, d, J 5.1 Hz); 7.23 (1H, s).

Step G: 2-amino-2-(2-fluoropyridin-4-yl)-1-[3-(trifluoromethyl)phenyl]ethanol

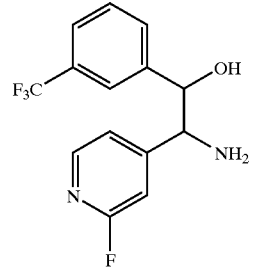

10% Palladium on carbon (3.0 g) was added to a solution of 1-(2-fluoropyridin-4-yl)-2-[3-(trifluoromethyl)phenyl] ethane-1,2-dione 1-oxime (8.0 g, 27 mmol) in ethanol (400 mL) at ambient temperature. The reaction vessel was vacuum purged with hydrogen and vigorously stirred for 10 hrs. After the reaction was complete, the solution was filtered through a pad of celite, and concentrated to give a yellow solid. The residue could be purified by recrystalization from methylene chloride and hexane. Alternatively, non polar impurities could be removed by filtration though silica gel starting with 5% methanol in methylene chloride to 5% methanol, 0.5% ammonium hydroxide in methylene chloride. Colorless solid (91%):

mp 128–129° C.; $^1$H NMR (300 MHz, CD$_3$OD) δ 8.01 (d, J=5.0 Hz, 1H, Ar), 7.53 (m, 1H, Ar), 7.49 (m, 2H, Ar), 7.43 (s, 1H, Ar), 7.06 (d, J=5.0 Hz, 1H, Ar), 6.86 (s, 1H, Ar), 4.96 (d, J=5.0 Hz, 1H, CH), 4.12 (d, J=5.0 Hz, 1H, CH).

Step H: 2-(2-fluoropyridin-4-yl)-2-(methylamino)-1-[3-(trifluoromethyl)phenyl]-ethanol

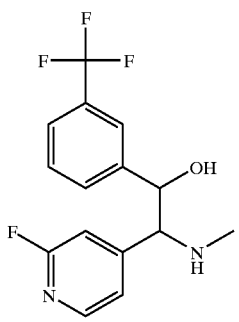

2-amino-2-(2-fluoropyridin-4-yl)-1-[3-(trifluoromethyl)phenyl]ethanol (6 g, 20 mmol) was dissolved in ethyl formate (80 mL) and heated to reflux for 10 hrs under an argon atmosphere. The reaction mixture was cooled to ambient temperature and concentrated to yield (99% pure by HPLC) the formamide. Colorless oil: $^1$H NMR (300 MHz, CD$_3$OD) δ 8.06 (m, 2H, Ar), 7.55 (m, 3H, Ar), 7.05 (m, 1H, Ar), 5.22 (d, J=5.7 Hz, 1H, CH), 5.10 (d, J=5.7 Hz, 1H, CH). The formamide was azeotroped with toluene (2×100 mL) to remove trace amounts of ethyl formate and water. Reduction to the desired compound was carried out by drop-wise addition of borane-tetrahydrofuran complex (60 mL of a 1.0 M solution in THF, 60 mmol) to a solution the formylated product (20 mmol) in THF (60 mL) at ambient temperature. After 1 hr, the reaction was quenched by slow addition of the organic mixture to a vigorously stirring solution of aqueous hydrochloric acid (2.0 M, 500 mL). Stirring was continued for 3 h to assure complete dissociation of boron with product. A solution of aqueous sodium hydroxide (10 M) was then added until a pH of 11 was achieved. The resulting mixture was extracted with ethyl acetate (2×300 mL), dried (sodium sulfate), and concentrated. The resulting residue was purified by filtration though a pad of silica gel (using 5% methanol and 0.5% ammonium hydroxide mixture in methylene chloride). Colorless solid (89%): mp 99–102° C.; $^1$H NMR (300 MHz, CD$_3$OD) δ 7.99 (d, J=5.1 Hz, 1H, Ar), 7.50 (m, 1H, Ar), 7.45 (m, 2H, Ar), 7.38 (s, 1H, Ar), 7.02 (m, 1H, Ar), 6.83 (s, 1H, Ar), 5.09 (d, J=4.8 Hz, 1H, CH), 3.85 (d, J=4.8 Hz, 1H, CH), 2.22 (s, 3H, CH$_3$).

Step I: benzyl 4-{[{1-(2-fluoropyridinyl)-2-hydroxy-2-[3-(trifluoromethyl)phenyl]-ethyl}(methyl)amino]carbonyl}piperidine-1-carboxylate:

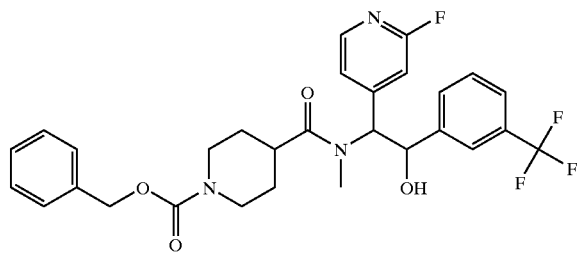

1-Ethyl-3-(3-dimethylaminopropyl)carbodiimide hydrochloride (1.47 g, 5.1 mmol) was added to a solution of 2-(2-fluoropyridin-4-yl)-2-(methylamino)-1-[3-(trifluoromethyl)phenyl]ethanol (1.60 g, 5.1 mmol), N-benzyloxycarbonyl piperidin-4-carboxylic acid (1.37 g, 5.2 mmol), triethylamine (3.5 mL, 25 mmol), and 1-hydroxy-7-azabenzotriazole (717 mg, 5.4 mmol) in dimethyl formamide (50 mL) at ambient temperature. After 1 hr stirring at ambient temperature, ethyl acetate was added (200 mL) followed by aqueous citric acid (50 mL of a 10% solution). The organic layer was then washed with aqueous sodium bicarbonate (100 mL of a sat. solution) and water (3×50 mL), dried (sodium sulfate), filtered, and concentrated. The crude residue was passed though a pad a silica gel (50% ethyl acetate in hexane) to remove minor impurities, and taken to the next step. Colorless oil (90%): $^1$H NMR (300 MHz, CD$_3$OD) δ 8.18 (d, J=5.4 Hz, 1H, Ar), 7.75 (m, 2H, Ar), 7.56 (m, 2H, Ar), 7.40 (m, 1H, Ar), 7.33 (m, 6H, Ar), 5.89 (d, J=9.9 Hz, 1H, CH), 5.45 (d, J=9.9 Hz, 1H, CH), 5.08 (s, 2H, CH$_2$), 4.06 (m, 1H, CH$_2$), 3.88 (m, 1H, CH$_2$), 2.77 (s, 3H, CH$_3$), 2.69 (m, 1H, CH$_2$), 2.51 (m, 1H, CH$_2$), 1.47 (m, 2H, CH$_2$), 0.93 (m, 2H, CH$_2$).

Step J: benzyl 4-{1-methyl-5-(2-oxo-1,2-dihydropyridin-4-yl)-4-[3-(trifluoromethyl)-phenyl]-1H-imidazol-2-yl}piperidine-1-carboxylate

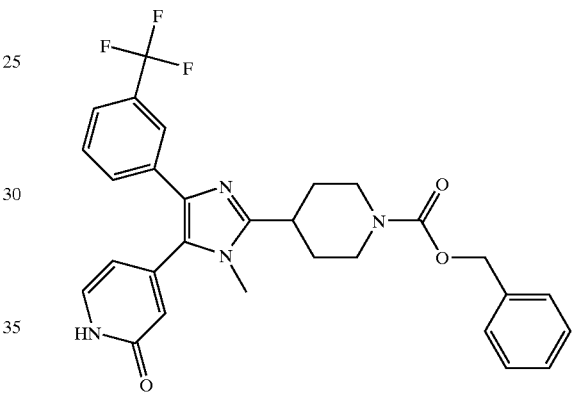

Oxalyl chloride (0.97 mL, 11 mmol) was added to a solution of dimethyl sulfoxide (0.98 mL, 14 mmol) in methylene chloride (50 mL) at −78° C. After 20 min. at −78° C., the product of step I (approx. 5.1 mmol from previous reaction) in methylene chloride (10 mL) was added and the reaction solution was stirred at −78° C. for 2 hrs. Triethylamine (2.3 mL, 17 mmol) was added and the cooling bath was removed. The solution was diluted with ethyl acetate (150 mL), washed with aqueous ammonium chloride (1×75 mL) and brine (1×75 mL), dried (sodium sulfate), and concentrated. Some non-polar impurities were removed by passing the residue through silica gel, eluting with 50% ethyl acetate in hexane. 0.298 g (0.554 mmol) of the ketone was then dissolved in acetic acid (5 mL), ammonium acetate (854 mg, 11.1 mmol) added and the mixture heated to reflux for 1.5 h. The reaction mixture was cooled, poured into ice/NH4Oh and extracted with ethyl acetate. The organic layer was washed with water and brine, dried over anhydrous sodium sulfate and the solvent evaporated to give the crude product, purified by flash column chromatography (95:5:0.5 DCM:MeOH:NH$_4$OH to give the pyridone (250 mg).: $^1$H NMR (300 MHz, CD$_3$OD) δ 7.73 (s, 1H), 7.63 (d, 1 H), 7.3–7.55 (m, 8H), 6.50 (s, 1H), 6.28 (dd, 1H), 5.15 (s, 2H), 4.37 (m, 2 H), 3.61 (s, 3H), 3.00 (m, 3H), 1.99 (m, 4H, CH$_2$).

Step K: 4-{1-methyl-2-piperidin-4-yl-4-[3-(trifluoromethyl)phenyl]-1H-imidazol-5-yl}pyridin-2(1H)-one

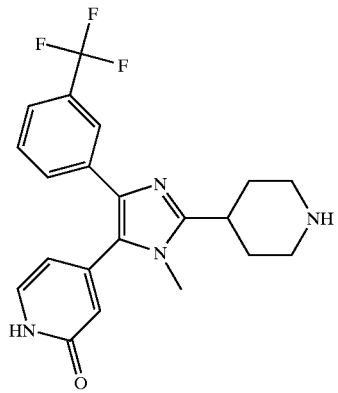

Benzyl 4-{1-methyl-5-(2-oxo-1,2-dihydropyridinyl)-4-[3-(trifluoromethyl)phenyl]-1H-imidazol-2-yl}piperidine-1-carboxylate (250 mg, 0466 mmol) in isopropanol (10 mL) was hydrogenated under 1 atm. of hydrogen over 10% Pd/C (100 mg) for 18 h, filtered and concentrated to give the crude product purified by flash column chromatography (90:10:1 DCM:MeOH:NH4OH to give the title compound (40 mg).
MS (M+1) 403.26

Step L: 3-methyl-2-piperidin-4-yl-10-(trifluoromethyl)-3,6-dihydro-7H-benzo[h]imidazo[4,5-f]isoquinolin-7-one

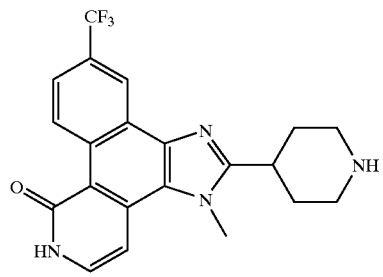

A 1 mM stock solution of 4-{1-methyl-2-piperidin-4-yl-4-[3-(trifluoro-methyl)phenyl]-1H-imidazol-5-yl}pyridin-2(1H)-one in DMSO was placed in a borosilicate glass vial and photolyzed under ambient temperature and atmosphere in a Rayonet photochemical reactor equipped with four 350 nm bulbs for 40 minutes. The reaction was found to be complete at that point as assessed by RPHPLC. MS (M+1) 401.1

EXAMPLE 42

2-Phenyl-3,6-dihydro-7H-imidazo[4,5-f]-2,9-phenanthrolin-7-one

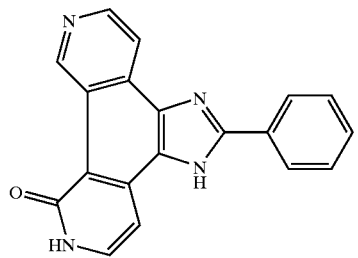

Step A: tert-Butyl 4-[2-oxo-2-(4-pyridinyl)ethyl]-2-pyridinylcarbamate

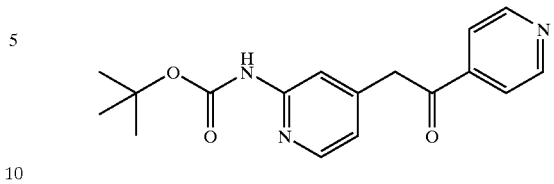

Tert-butyl 4-methyl-2-pyridinylcarbamate (Ihle, N. C.; Krause, A. E.; *J. Org. Chem.*, 1996, 61(14):4810–4811; 10 g, 48.0 mmol) was dissolved in 100 mL THF and cooled to −78° C. under argon and was treated with n-butyllithium (2.5-M in hexanes, 48.0 mL, 120 mmol) such that the internal temperature did not exceed −50° C. The reaction was warmed to 20° C. for 20 min. then was recooled to −78° C. and ethyl isonicotinate (10.79 mL, 72.0 mmol) was added neat and the reaction again was warmed to 20° C. and stirred 45 minutes. The reaction was quenched with sat. NaHCO$_3$ and extracted with ethyl acetate. The organics were dried over Na$_2$SO$_4$, filtered and concentrated under reduced pressure to give a red-orange oil which was purified by silica gel chromatography, eluting from 50% ethyl acetate in hexanes to 100% ethyl acetate to afford 7.56 g (50%) of the titled compound as a yellow oil.

$^1$H NMR (300 MHz, δ, CDCl$_3$): 8.84, (dd, J=3.90, 1.46 Hz, 2H, Pyr-H), 8.22–8.18 (m, 1H, Pyr-H), 7.91 (brs, 1H, Pyr-H), 7.76 (dd, J=3.90, 1.46 Hz, 2H, Pyr-H), 6.85 (d, J=5.13 Hz, 1H, Pyr-H), 4.28 (s, 2H, CH$_2$), 1.52 (s, 9H, (CH$_3$)$_3$).

Step B: tert-Butyl 4-[2-phenyl-4-(4-pyridinyl)-1H-imidazol-5-yl]-2-pyridinyl-carbamate

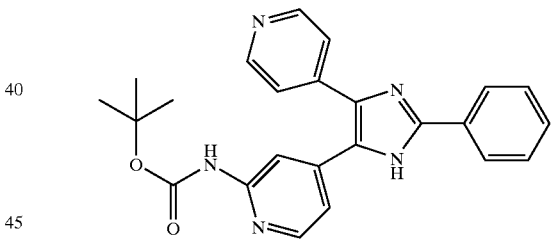

The tert-butyl 4-[2-oxo-2-(4-pyridinyl)ethyl]-2-pyridinylcarbamate (2.40 g, 7.66 mmol) was suspended in dry DMSO (20 mL) under argon and was treated with N-bromosuccinimide (NBS, 1.50 g, 8.42 mmol). At 40–60 seconds after NBS addition, the color of the reaction went from yellow to dark brown then benzamidine (3.68 g, 30.66 mmol) was added in a single portion. After 90 minutes, the reaction was diluted with ethyl acetate and was washed with sat. K$_2$CO$_3$, water and brine then was dried over Na$_2$SO$_4$, filtered and concentrated under reduced pressure with ~20 g silica gel and then purified by silica gel chromatography, eluting with 0.1% triethylamine in ethyl acetate. Trituration of the purest fractions from the chromatography in hot ether gave 88 mg (3%) of the titled compound as a yellow solid.

MS (EI) M/Z=414. $^1$H NMR (300 MHz, δ, CD$_3$OD): 8.53 (d, J=5.86 Hz, 2H, Pyr-H), 8.23 (d, J=5.38 Hz, 1H, Pyr-H), 8.05 (s, 2H, Pyr-H), 8.02 (s, 1H, Pyr-H), 7.62 (d, J=5.62 Hz, 2H, Ph-H), 7.54–7.44 (m, 3H, Ph-H), 7.17 (brs, 1H, Pyr-H), 1.50 (s, 9H, (CH$_3$)$_3$).

Step C: 4-[2-Phenyl-4-(4-pyridinyl)-1H-imidazol-5-yl]-2-pyridinamine

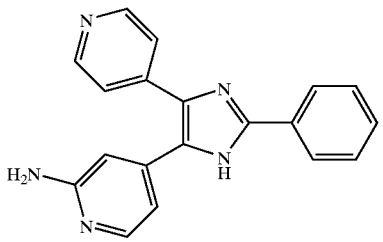

Trifluoroacetic acid (8 mL) was added to tert-butyl 4-[2-phenyl-4-(4-pyridinyl)-1H-imidazol-5-yl]-2-pyridinylcarbamate in dichloromethane (10 mL) and after 42 h, the volatiles were removed under reduced pressure. The residue was diluted with ethyl acetate and was washed with st. $K_2CO_3$, dried over $Na_2SO_4$, filtered and concentrated in vacuo to give a yellow solid which was purified by silica gel chromatography, eluting with 95 $CH_2Cl_2$:5 $CH_3OH$:0.5 $NH_4OH$ to afford the 258 mg (50%) of the titled compound as a yellow solid.

Step D: 4-(2-phenyl-4-pyridin-4-yl-1H-imidazol-5-yl)pyridin-2(1H)-one

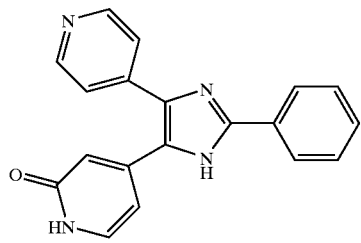

The 4-[2-phenyl-4-(4-pyridinyl)-1H-imidazol-5-yl]-2-pyridinamine (86 mg, 0.27 mmol) was dissolved in 1.5 mL water containing 0.1 mL conc. Sulfuric acid and was treated with $NaNO_2$ (24 mg, 0.38 mmol) and stirred 60 minutes. Another 7 mg $NaNO_2$ (0.01 mmol) was added and the reaction was heated over a steam bath for 5 min. then was cooled to r.t. The reaction was basified with sat. $NaHCO_3$ and was extracted with ethyl acetate. The combined organics were dried over $Na_2SO_4$, filtered and concentrated under reduced pressure to give a pale yellow solid which was triturated in ether to give 27 mg (31%) of the title compound as a pale yellow solid.

MS (EI) M/Z=315. $^1$H NMR (300 MHz, δ, DMSO-$d_6$): 13.03 (brs, 1H, Pyr-H), 11.61 (brs, 1H, imidazole-H), 8.66 (d, J=5.13 Hz, 1H, Pyr-H), 8.55 (d, J=5.19 Hz, 1H, Pyr-H), 8.08 (t, J=7.33 Hz, 2H, Pyr-H), 7.57–7.32 (m, 6H, Pyr-H, Ar-H), 6.56 (s) 6.44 (s) (1H total, Pyr-H), 6.32–6.30 (m) 6.16–6.00 (m) (1H total, Pyr-H).

Step E: 2-phenyl-3,6-dihydro-7H-imidazo[4,5-f]-2,9-phenanthrolin-7-one

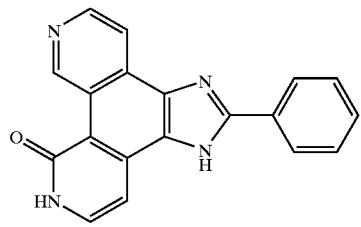

A 10.6 μL sample of a 9.4 mM DMSO stock of 4-(2-phenyl-4-pyridin-4-yl-1H-imidazol-5-yl)pyridin-2(1H)-one was diluted to 100 μL by the addition of 89.4 μL of DMSO to give a 1 mM compound stock. This material was then placed in a borosilicate glass vial and photolyzed under ambient temperature and atmosphere in a Rayonet photochemical reactor equipped with four 350 nm bulbs for 40 minutes. The reaction was found to be complete at that point as assessed by RPHPLC. UV/Vis (lmax=309 nm, shoulder at 350 nm). MS (M+H) 313.

EXAMPLE 43

Benzyl 4-[7-oxo-10-(trifluoromethyl)-6,7-dihydro-3H-benzo[h]imidazo[4,5-f]isoquinolin-2-yl]piperidine-1-carboxylate

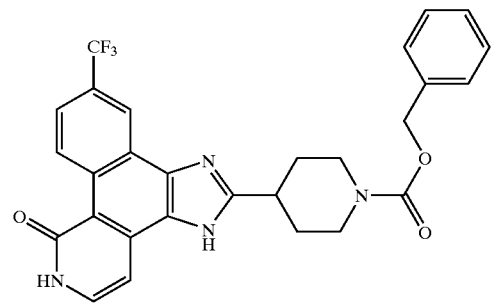

Step A: benzyl 4-{5-(2-oxo-1,2-dihydropyridin-4-yl)-4-[3-(trifluoromethyl)phenyl]-1H-imidazol-2-yl}piperidine-1-carboxylate

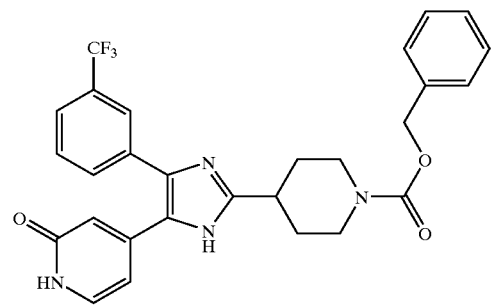

A mixture of the 1-(2-fluoropyridin-4-yl)-2-(3-trifluoromethylphenyl)-ethane-1,2-dione 1-oxime (EXAMPLE 41, Step F) (7.3 g, 23.3 mmol), N-benzyloxycarbonyl piperidin-4-carboxaldehyde (6.36 g, 25.7 mmol) and ammonium acetate (27 g, 350 mmol) in acetic acid (100 mL) was heated to reflux for 6 h. The reaction mixture was cooled, poured into ice/NH4OH and extracted with ethyl acetate. The organic layer was washed with water and brine, dried over anhydrous sodium sulfate and the solvent evaporated to give the crude product. 400 mg of this crude product was dissolved in methanol (5 mL) and TiCl3 (3 mL of 10% solution in 20% HCl) added. Reaction mixture stirred for 30 min at room temperature then saturated aqueous sodium bicarbonate solution added carefully and the mixture stirred vigorously until a white precipitate had formed. The solution was then partitioned with EtOAc and the organic layer washed with water and brine, dired over sodium sulfate and the solvent evaporated. The crude product was purified by flash column chromatography on silica (33–50% EtOAc hexane) to give the title compound (210 mg).

CHN Calc. C, 64.36%; H, 4.82%; N, 10.72%; Found C, 64.29%; H, 4.82%; N, 10.57%.

Step B: Benzyl 4-[7-oxo-10-(trifluoromethyl)-6,7-dihydro-3H-benzo[h]imidazo-[4,5-f]isoquinolin-2-yl]piperidine-1-carboxylate

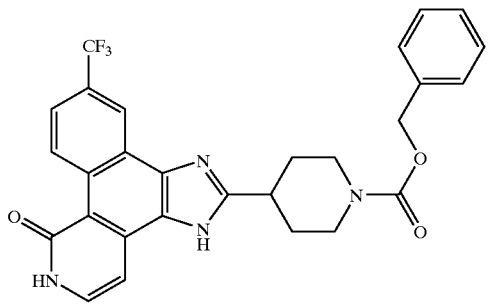

A 1 mM stock solution of benzyl 4-{5-(2-oxo-1,2-dihydropyridin-4-yl)-4-[3-(trifluoromethyl)phenyl]-1H-imidazol-2-yl}piperidine-1-carboxylate in DMSO was placed in a borosilicate glass vial and photolyzed under ambient temperature and atmosphere in a Rayonet photochemical reactor equipped with four 350 nm bulbs for 40 minutes. The reaction was found to be complete at that point as assessed by RPHPLC.

EXAMPLE 44

Assay For Jak Family Protein Kinase Activity

Materials. Streptavidine.allophycocyanin conjugate (SA.APC) and Europium.ecryptate (Eu.K) were from Packard Instrument Company. Eu.K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79–93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

Jak family kinase expression. Jak3, Tyk2 and Jak2 kinase domains with N-terminal "Flag" affinity tags were expressed in Sf9 cells using standard baculovirus methods. The human Jak3 gene was provided by Dr. John J. O'Shea (NDI). The human Tyk2 gene was provided by Dr. Sandra Pellegrini (Insitut Pasteur). Human Jak2 kinase domain was cloned from a MOLT4 cDNA library (Clonetech).

Assay for Jak family protein kinase activity. Tyrosine kinase activity was measured by detection of the tyrosine phosphorylated peptide amino hexanoyl biotin-EQEDEPEGDYFEWLE-$NH_2$ (S, hereafter) detected by homogenous time resolved fluorescence (HTRF) using a europium labeled antibody to phosphotyrosine (pY20). The Jak3(JH1) catalyzed phosphorylation reactions were carried out in kinase reaction buffer (KB) (50 mM Hepes pH 7.0, 0.01 M $MgCl_2$, 1 mM DTT, 1 mg/ml BSA) 1 μM S, and 200 pM Jak3(JH1). Reactions were run at ambient temperature and quenched with an equal volume of quench buffer (QB) (50 mM Hepes pH 7.0, 50 mM EDTA, 100 mM KF). The quenched reactions were mixed with an equal volume of 0.5 μM.SAAPC conjugate and 0.6 nM Eu.K conjugated pY20. This mixture was incubated at ambient temperature for at least 60 minutes and before detection of HTRF.

Cellular proliferation assays. CTLL-2 cells (ATCC) were maintained in 6% T-stim Culture Supplement (source of IL2) in RPMI-1640 supplemented with 10% fetal bovine serum, 1 mM sodium pyruvate, 50 μM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5 \times 10^5$/ml. The next day, cells were washed and plated at $0.2-1 \times 10^5$ cells/well in a 96 well tissue culture plate (CoStar). 0.05 ng/ml mouse recombinant IL2 (Pharmingen), with or without a test compound, or 20 ng/ml PMA (Sigma) and 1 μCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

What is claimed is:

1. A compound of fomula I:

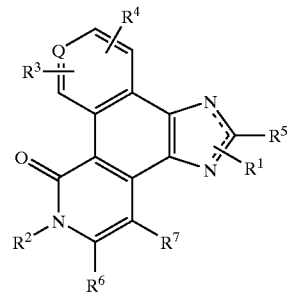

wherein one of the ═══ bond is a double bond, and the other is a single bond;

Q is N or C;

$R^1$ is attached to the nitrogen atom having the available valence, and is selected om hydrogen, $C_{1-6}$alkyl, $C_{2-6}$alkenyl, $C_{3-6}$cycloalkyl, aryl-$C_{1-3}$alkyl, and aryl wherein said akyl, alkenyl, cycloalkyl, and aryl are optionally substituted with one to three groups independently selected from X;

$R^2$ is a group selected from $R^1$;

$R^3$, $R^4$, $R^6$ and $R^7$ are independently selected from hydrogen, X, $C_{2-6}$alkenyl and $C_{3-6}$cycloalkyl wherein said alkenyl and cycloalkyl are optionally substituted with one to three groups independently selected from X;

$R^5$ is selected from hydrogen, $C_{1-6}$alkyl, $C_{2-6}$alkenyl, Cy, and Cy-$C_{1-3}$alkyl, wherein said alkyl, alkenyl, and Cy are optionally substituted with one to three groups independently selected from X;

Cy is selected from cycloalkyl, heterocyclyl, aryl, and heteroaryl;

X is selected from:

halo,

CN, $OR^a$, $C_{1-6}$perfluoroalkyl, $C(O)R^a$, $C(O)OR^a$, $C(O)NR^bR^c$, $NR^bR^c$, $NHR^bNHR^b$, $NHC(O)R^a$, $NHC(O)OR^a$, phenyl wherein phenyl is optionally substituted with one to three groups independently selected from $R^x$, $C_{1-6}$alkyl optionally substituted with OH, $C_{3-7}$cycloalkyl, phenyl, or heterocyclyl, wherein phenyl is optionally substituted with one to three groups independently selected from $R^x$, and wherein said heterocyclyl is optionally substituted with one to three groups independently selected from $R^y$, heterocyclyl wherein said heterocyclyl is optionally substituted with one to three groups independently selected from $R^y$, $S(O)_n R^a$, wherein n is 0, 1 or 2 and $SO_2 NHR^a$;

$R^a$, $R^b$ and $R^c$ are independently selected from hydrogen, $C_{1-6}$alkyl, $C_{2-6}$alkenyl, $C_{2-6}$alkynyl, Cy and Cy-$C_{1-3}$alkyl, wherein Cy is optionally substituted with one to three groups selected from $R^y$; or $R^b$ and $R^c$ together with the atom(s) to which they are attached form a heterocyclic ring of 4 to 7 members containing 0–2 additional heteroatoms independently selected from oxygen, sulfur and N—$R^e$;

$R^e$ is selected from hydrogen, $C_{1-6}$alkyl, Cy and Cy-$C_{1-3}$alkyl;

$R^x$ is selected from halo, phenyl, CN, $NO_2$, OH, $OC_{1-6}$alkyl, $C_{1-6}$alkyl, $NH_2$, $C_{1-6}$alkyl, $N(C_{1-6}$alkyl$)_2$, C(O)$C_{1-6}$alkyl, C(O)O$C_{1-6}$alkyl, C(O)NH$C_{1-6}$alkyl, C(O)N($C_{1-6}$alkyl$)_2$, NHC(O)$C_{1-6}$alkyl;

$R^y$ is a group selected from $R^x$, oxo, $C_{1-6}$alkyl substituted with $C_{3-7}$cycloalkyl and C(O)OCH$_2$-phenyl;

or a pharmaceutically acceptable salt thereof.

2. A compound of claim 1 wherein $R^1$ is selected from hydrogen, $C_{1-6}$alkyl, $C_{3-6}$cycloalkyl and aryl-$C_{1-3}$alkyl wherein alkyl, cycloalkyl and aryl are optionally substituted with one or two groups independently selected from X.

3. A compound of claim 1 wherein $R^3$ and are $R^4$ are independently selected from hydrogen, halogen and trifluoromethyl.

4. A compound of claim 1 wherein Q is C and one of $R^3$ and $R^4$ is halogen or trifluoromethyl at the 9-position, and the other is H, halogen or trifluoromethyl.

5. A compound of claim 1 wherein $R^5$ is selected from $C_{1-6}$alkyl and Cy wherein each is optionally substituted with one to three groups independently selected from X.

6. A compound of claim 1 wherein $R^5$ is phenyl optionally substituted with one to three groups independently selected from X.

7. A compound of claim 1 wherein Q is C.

8. A compound of claim 1 wherein Q is N.

9. A pharmaceutical composition comprising a compound of claim 1 and a pharmaceutically acceptable carrier.

\* \* \* \* \*